(12) United States Patent
Sakanyan et al.

(10) Patent No.: US 7,186,525 B2
(45) Date of Patent: Mar. 6, 2007

(54) METHODS OF RNA AND PROTEIN SYNTHESIS

(75) Inventors: Vehary Sakanyan, Orvault (FR); Marina Snapyan, Bures sur Yvette (FR); Anahit Ghochikyan, Huntington Beach, CA (US); Francoise-Michèle Lecocq, Nantes (FR)

(73) Assignee: Universite de Nantes, Nantes Cedex (FR)

( * ) Notice: Subject to any disclaimer, the term of this patent is extended or adjusted under 35 U.S.C. 154(b) by 0 days.

(21) Appl. No.: 10/764,581

(22) Filed: Jan. 27, 2004

(65) Prior Publication Data

US 2005/0032086 A1 Feb. 10, 2005

Related U.S. Application Data

(63) Continuation of application No. PCT/EP02/09423, filed on Jul. 26, 2002.

(30) Foreign Application Priority Data

Jul. 27, 2001 (EP) ................... 01402049

(51) Int. Cl.
C12P 21/02 (2006.01)
C12P 19/34 (2006.01)
C12N 1/06 (2006.01)
C07H 21/02 (2006.01)

(52) U.S. Cl. ................. 435/69.1; 435/91.5; 435/252.3; 536/25.3

(58) Field of Classification Search .................... None
See application file for complete search history.

(56) References Cited

FOREIGN PATENT DOCUMENTS

| WO | WO 98/24891 | 6/1998 |
| WO | WO 00/63413 | 10/2000 |

OTHER PUBLICATIONS

Bowrin et al. The alpha subunit of RNA polymerase specifically inhibits expression of the porin genes ompF and ompC in vivo and in vitro in *Escherichia coli*. FEMS Microbiol Lett. vol. 115, No. 1, pp. 1-6, Jan. 1994.*

Lesley et al. J Biol Chem. vol. 266, No. 4, pp. 2632-2638, Feb. 1991.*

Bowrin, Brissette and Inouye. Two transcriptionally active OmpR mutants that do not require phosphorylation by EnvZ in an *Escherichia coli* cell-free system. J Bacteriol. vol. 174, No. 20, pp. 6685-6687, Oct. 1992.*

Savchenko et al. The *Bacillus stearothermophilus* argCJBD operon harbours a strong promoter as evaluated in *Escherichia coli* cells. Gene. vol. 212, No. 2, pp. 167-177, Jun. 1998.*

Fujita et al. Reconstitution of RNA polymerase. Methods Enzymol. vol. 273, pp. 121-130, 1996.*

Xue et al. Purification and initial characterization of RNA polymerase from *Thermus thermophilus* strain HB8. Biochemistry. vol. 39, No. 46, pp. 14356-14362, Nov. 2000.*

Uptain et al. *Escherichia coli* RNA polymerase terminates transcription efficiently at rho-independent terminators on single-stranded DNA templates. Proc Natl Acad Sci U S A. vol. 94, No. 25, pp. 13548-13553, Dec. 1997.*

Inouye et al. Up-promoter mutations in the lpp gene of *Escherichia coli*. Nucleic Acids Research, vol. 13, No. 9, pp. 3101-3110, 1985.*

Carbonetti et al., "Effect of Mutations Causing Overexpression of RNA Polymerase α Subunit on Regulation of Virulence Factors in *Bordetella pertussis*", Journal of Bacteriology, vol. 176, No. 23, pp. 7267-7273, 1994, XP-001022285.

Russo et al., "Alpha: The Cinderella Subunit of RNA Polymerase", Journal of Biological Chemistry, American Society of Biological Chemists, vol. 267, NO. 21, pp. 14515-14518, 1992, XP-000864425.

Gourse et al., "UPs and downs in bacterial transcription initiation: the role of the alpha subunit of RNA polymerase in promoter recognition", Molecular Microbiology, vol. 37, No. 4, pp. 687-695, 2000, XP-002182862.

Estrem et al., "Identification of an UP element consensus sequence for bacterial promoters", Proc. Natl. Acad. Sci. USA; vol. 95, pp. 9761-9766, 1998, XP-002182863.

* cited by examiner

*Primary Examiner*—Celine Qian
*Assistant Examiner*—Jennifer Dunston
(74) *Attorney, Agent, or Firm*—Young & Thompson

(57) ABSTRACT

The present invention relates to methods for RNA and/or protein synthesis using in vitro or in vivo expression systems. More specifically, the present invention provides a method for RNA and/or protein synthesis characterized in that the concentration of alpha subunit of RNA polymerase, but not of other subunits, is increased in the cellular or cell-free system, comparing to its natural concentration existing in the cellular or cell-free system.

28 Claims, 11 Drawing Sheets

SEQUENCE LISTING

<160> NUMBER OF SEQ ID NOS: 17

<210> SEQ ID NO 1
<211> LENGTH: 19
<212> TYPE: DNA
<213> ORGANISM: Bacillus stearothermophilus

<400> SEQUENCE: 1
catagactta gggaggggc                                                   19

<210> SEQ ID NO 2
<211> LENGTH: 42
<212> TYPE: DNA
<213> ORGANISM: Bacillus stearothermophilus

<400> SEQUENCE: 2
atgatgatga tgatgatgca tatgttcccc ctcacccgta tg                         42

<210> SEQ ID NO 3
<211> LENGTH: 22
<212> TYPE: DNA
<213> ORGANISM: Bacillus stearothermophilus

<400> SEQUENCE: 3
cctcgaaaat tattaaatat ac                                               22

<210> SEQ ID NO 4
<211> LENGTH: 22
<212> TYPE: DNA
<213> ORGANISM: Bacillus stearothermophilus

<400> SEQUENCE: 4
acatttgatt ttatttttat ac                                               22

<210> SEQ ID NO 5
<211> LENGTH: 42
<212> TYPE: DNA
<213> ORGANISM: Thermotoga maritima

<400> SEQUENCE: 5
atgcatcatc atcatcatca taaaaaaatc gaagtggacc tc                         42

<210> SEQ ID NO 6
<211> LENGTH: 19
<212> TYPE: DNA
<213> ORGANISM: Thermotoga maritima

<400> SEQUENCE: 6
gaacgaaaca ccctccgcc                                                   19

<210> SEQ ID NO 7
<211> LENGTH: 45
<212> TYPE: DNA
<213> ORGANISM: Thermotoga maritima

<400> SEQUENCE: 7
atgcatcatc atcatcatca tatcgatgaa ataaaatctg gaaag                      45

<210> SEQ ID NO 8
<211> LENGTH: 18
<212> TYPE: DNA
<213> ORGANISM: Thermotoga maritima

```
<400> SEQUENCE: 8
ctcgctggag gatcacac                                              18

<210> SEQ ID NO 9
<211> LENGTH: 40
<212> TYPE: DNA
<213> ORGANISM: Thermotoga maritima

<400> SEQUENCE: 9
atgcatcatc atcatcatca tccgaaatcg gtgagagcag                      40

<210> SEQ ID NO 10
<211> LENGTH: 22
<212> TYPE: DNA
<213> ORGANISM: Thermotoga maritima

<400> SEQUENCE: 10
ctccacgtgt aaatgtacag tg                                         22

<210> SEQ ID NO 11
<211> LENGTH: 40
<212> TYPE: DNA
<213> ORGANISM: Thermotoga maritima

<400> SEQUENCE: 11
atgcatcatc atcatcatca tccaacaata gaagatgtcg                      40

<210> SEQ ID NO 12
<211> LENGTH: 21
<212> TYPE: DNA
<213> ORGANISM: Thermotoga maritima

<400> SEQUENCE: 12
gaccactcga tctgaacatc c                                          21

<210> SEQ ID NO 13
<211> LENGTH: 27
<212> TYPE: DNA
<213> ORGANISM: E. coli

<400> SEQUENCE: 13
gacaccatgg agggttctgt gacagag                                    27

<210> SEQ ID NO 14
<211> LENGTH: 27
<212> TYPE: DNA
<213> ORGANISM: E. coli

<400> SEQUENCE: 14
ccgctcgagc tcgtcagcga tgcttgc                                    27

<210> SEQ ID NO 15
<211> LENGTH: 23
<212> TYPE: DNA
<213> ORGANISM: E. Coli

<400> SEQUENCE: 15
catgccatgg tgcttggcaa acc                                        23

<210> SEQ ID NO 16
<211> LENGTH: 27
<212> TYPE: DNA
```

```
-continued

<213> ORGANISM: E. Coli

<400> SEQUENCE: 16
ccgctcgaga cgagtgccgt aaacgac                                          27

<210> SEQ ID NO 17
<211> LENGTH: 126
<212> TYPE: DNA
<213> ORGANISM: Bacillus stearothermophilus

<400> SEQUENCE: 17
catagactta gggagggca agaaaaaaat cctcgaaaat tattaaatat acatttgatt       60
ttatttttat acagtattat aatgagaact acatgaggca tacgggtgag ggggaacatg    120
atgaac                                                               126
```

METHODS OF RNA AND PROTEIN SYNTHESIS

Figure 1:
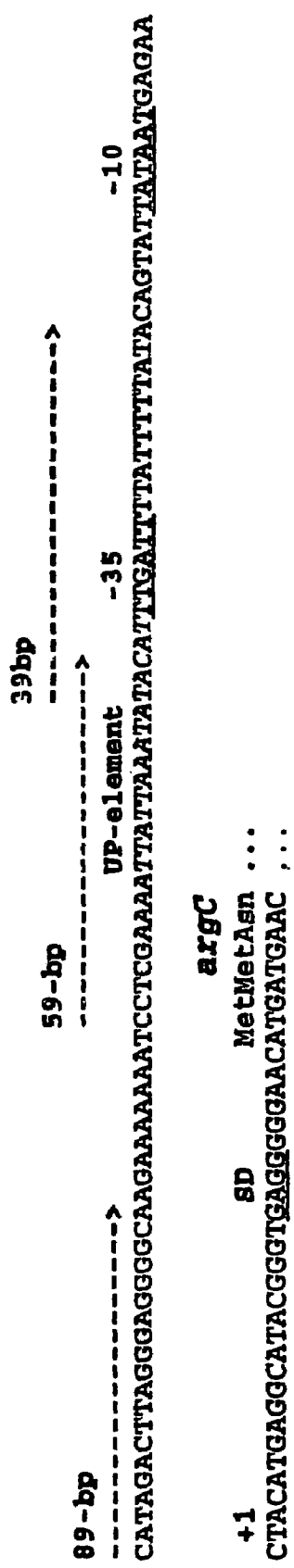

This is a continuation of International Application PCT/EP02/09423 filed on 26 Jul. 2002, which designated the United States of America.

FIELD OF THE INVENTION

The present invention relates to improved methods for RNA and/or protein synthesis using in vitro or in vivo expression systems. More specifically, the present invention provides a method for RNA and/or protein synthesis in cellular or cell-free expression systems characterized in that the concentration of α subunit of RNA polymerase, but not other subunits thereof, is increased in said cellular or cell-free system, comparing to its natural concentration existing in said cellular or cell-free system.

BACKGROUND OF THE INVENTION

Gene expression and production of a desired protein in a heterologous cytoplasmic environment is a great advantage of modern biology. Many vector-host systems have been developed to achieve high yield of protein synthesis.

In particular, many proteins of interests are produced by expression systems as recombinant proteins in order to improve the yield of synthesis, to rationalize the production, to facilitate their production or to limit the risk of contamination by accompanying compounds.

Examples of recombinant biomolecules of interests in biotechnology are antigens, antibodies and fragments thereof for vaccines, enzymes in medicine or agro-food industry, hormones, cytokines or growth factor in medicine or agronomy.

The rapid development of high throughput technologies needs also to provide cells expressing protein or polypeptide of interest, such as an antigen, an antibody, a receptor for identifying ligands, agonists or antagonists thereof.

Synthesis of specific RNAs can also be useful for their subsequent use in protein synthesis, in diagnosis or in anti-sense therapeutic approach for example.

Usual methods of recombinant protein synthesis include in vivo expression of recombinant genes from strong promoters in host cells, such as bacteria, yeast or mammalian cells or in vitro expression from a DNA template in cell-free extracts, such as the S30 system-based method developed by. Zubay (1973), the rabbit reticulocyte system-based method (Pelham and Jackson, 1976, *Eur. J. Biochem.*, 67: 247–256) or wheat germ lysate system-based method (Roberts and Paterson, 1973, *PNAS*, 70: 2330–2334).

One advantage of a cell-free system is that it allows the synthesis of proteins harmful for host cells (Zubay, 1973;). Cell-free synthesis has been used as an essential component for translation-based screening in polysome display, truncation test, scanning saturation mutagenesis, site-specific incorporation of unnatural amino acids into proteins, stable-isotope labeling of proteins. Both circular and linear exogenous DNAs can be used as templates for protein synthesis and a high yield of protein synthesis can be reached from strong phage promoters in bacterial cell-free system ( ). However, many unknown factors affect the yield and the homogeneity of protein synthesis in a cell-free system and, therefore, a wide application is limited. Therefore, there is a need to improve the available methods for protein or RNA synthesis, especially with regard to the yield of synthesis and the homogeneity of production.

Actually, improvements at the different steps of gene expression are required to increase the yield of RNA or protein synthesis in an expression system. Nevertheless, the most crucial steps are the steps of transcription initiation and translation initiation. Therefore, the best known expression systems in the art are based on the use of strong transcriptional and translational signals. As an example, strong phage promoters are widely used for gene expression and protein production both in living cells or cell-free extracts (Studier et al., 1990).

If the different components involved in transcription and translation synthesis are well-known in the Art, the specific contribution of each component is still controversial. Since the steps of transcription and translation initiation are considered to be the rate-limiting steps in RNA or protein synthesis, fundamental mechanisms of these cellular process should be better understood. With regards to the step of transcription initiation, the RNA polymerase is the key enzyme either in cellular or in cell free system.

The *Escherichia coli* RNA polymerase core enzyme is assembled sequentially to a heterotetrapolymer in the following order: $\alpha > \alpha_2 > \alpha_2\beta > \alpha_2\beta\beta'$. Said core enzyme $\alpha_2\beta\beta'$ acquires the capacity to recognize and bind to specific sequences of promoter only after its association with exchangeable σ subunits, thereby forming the functionally active holoenzyme able to catalyse RNA synthesis (see for reviews, Gross et al., 1992). It has been shown, that the presence of AT-rich sequences located in promoters can increase mRNA synthesis in vitro in the absence of other added factors. Later, it has been revealed that the α subunit binds to a AT-rich sequence, known as a UP element, located upstream a −35 site of strong promoters (Ross et at., 1993). However, UP element appears to be present in other promoters as well (Estrem et al., 1998). The α subunit of the RNA polymerase (encoded by the rpoA gene is composed of two domains, an N-terminal domain (αNTD) and a C-terminal domain (αCTD), which are connected by a flexible protease sensible linker. The αNTD domain is necessary for RNA polymerase assembly whereas the αCTD domain is involved both, in DNA-binding and in specific interactions with a number of transcription factors, including cAMP receptor protein (CRP), OxyR, TyrR, GalR (Ishihama, 1993). More specifically, Jeon et al., have shown that the same αCTD protein region is involved in binding to UP element and to specific transcription factors (Jeon et al., 1997). Two α subunits bind in tandem to the UP element. The helix IV of the αCTD domain binds directly to some promoters (Ozolino et al., 2000). Analysis of UP elements in a library of random sequences allowed the selection of UP elements increasing in vivo transcription synthesis up to 330-fold (Gourse et al., 2000).

RNA synthesis is decreased in in vitro transcription system in presence of a reconstituted RNA polymerase, wherein the α subunit is mutated for binding to the UP-element as compared to RNA synthesis level obtained with the reconstituted holoenzyme with a wild-type α subunit (Gaal et al., 1996; Ross et al., 1998). However, the overexpressed *E. coli* RNA polymerase α subunit has been shown to inhibit overexpression of osmoregulatory porin genes ompF and ompC in cells and the purified α subunit added along with RNA polymerase inhibits synthesis from the ompF promoter in in vitro transcription system (Bowrin et al., 1994).

These last results show the major role of UP elements and probably, their interacting proteins, in the modulation of the level of mRNA synthesis in bacterial cells.

SUMMARY OF THE INVENTION

In the present invention, it has been surprisingly found that the α subunit of RNA polymerase can play a determinant role in increasing RNA and protein synthesis in cellular or cellfree expression systems, as compared to the other subunits of RNA polymerase.

Indeed, functional RNA polymerase holoenzymes of bacteria are composed of a precise stoechiometric ratio of two α, one β, one β' and one σ subunits. However, the present invention results from the finding that the increase in an expression system of α subunit concentration, with no change of the concentration of the other subunits, improves significantly the yield of mRNA synthesis, and by way of consequence, the yield of corresponding protein production.

Thus, the invention provides improved methods for RNA and protein synthesis that significantly increase the yield of any RNA or protein production either in in vivo or in vitro expression systems.

More specifically, the invention relates to an improved method for RNA or polypeptide synthesis from a DNA template comprising the steps of.
(a) providing a cellular or cell-free system enabling RNA or polypeptide synthesis from a DNA template, said DNA template comprising a promoter with at least one UP element,
(b) recovering said synthesized RNA or polypeptide, characterized in that the concentration in said cellular or cell-free system of α subunit of RNA polymerase, but not of other subunits of the like, is increased, comparing to its natural concentration existing in said cellular or cell-free system.

As used herein, the term "natural concentration" refers to the concentration of the RNA polymerase α subunit established in vivo in bacterial cells without affecting the growth conditions or to the concentration of the RNA polymerase α subunit in in vitro reconstituted holoenzyme from purified subunits.

The method of the invention is useful in particular for any purposes requiring the synthesis of a specific RNA. Especially, the RNA which is produced according to the method of the invention is useful, as mRNA for in vitro protein synthesis, as hybridization probes in diagnosis assays, as substrates for analysing processing reactions or RNA splicing. RNAs produced from in vivo cellular systems or in vitro cell-free systems are also useful for the production of specific proteins of interest (such as antigens for vaccines, hormones, enzymes, or other proteins of medical or commercial value, for example).

The increase of the concentration of the α subunit can refer, either to an increase of the concentration of an α subunit which is identical to the one initially present in the selected expression system, or to an α subunit which is different but which can associate with β, β' and σ subunits initially present in the expression system to form the holoenzyme. For example, said different α subunit can be a mutated form of the α subunit, initially present in the selected expression system or a similar form from a related organism, provided that the essential αCTD and/or αNTD domains are still conserved or a chimaeric from related organisms.

The α subunit used in the present invention is, for example, obtained from *E. coli*, *T. thermotoga*, *T. maritima* or *T. neapolitana*.

The term "polypeptide" or "protein" is used in the present text alternatively and refers to any amino-acid sequence.

In order to simplify the reading of the present text, as used herein, the term "DNA template" refers to a nucleic acid comprising the sequence corresponding to the RNA or encoding the protein of interest, to be synthesized by the method of the invention.

According to the invention, the DNA template further comprises at least the following elements:
 specific signals for transcription initiation comprising a promoter with an UP element;
 optionally, specific signals for transcription termination;
 optionally, specific signals for binding transcriptional activating proteins;
 an Open Reading Frame with an initiation codon and a stop codon encoding a protein of interest;
 specific signals for translation initiation and termination;
 optionally, a sequence in frame with said Open Reading Frame, encoding a tag for convenient purification or detection;

The selection of the different above-mentioned elements depends upon the selected expression system, and in particular, upon the eucaryotic or prokaryotic origin of the selected expression system.

As used herein, an UP DNA element refers to a specific AT-rich region sequence, generally around 18–20 bp long, located upstream a −35 promoter site, to which RNA polymerase holoenzyme binds via the two α subunits for initiation of transcription. In a preferred embodiment, the DNA template comprises a strong bacterial promoter with at least one UP element, preferentially, the promoter of the argC gene from *Bacillus stearothermophilus* or part thereof. Indeed, the present invention also results from the finding that the promoter of the argC gene from *B. stearothermophilus*, as a strong-bacterial promoter, is particularly efficient for use in expression systems when the concentration of α subunit is increased. A preferred part of the promoter of the argC gene from *B. stearothermophilus* is a 89 nucleotide sequence upstream the first nucleotide (+1) of argC mRNA.

In one specific embodiment of the method, said system enabling RNA or polypeptide synthesis from a DNA template is a cellular system. A cellular system is characterized in that it includes culture of recombinant host cells transformed with an appropriate vector containing the DNA template.

Any cellular system known in the Art can be used for the purpose of the invention. The one skilled in the Art will select the cellular system depending upon the type of RNA or protein to synthesize In one aspect of the invention, a cellular expression system comprises the culture of transfected eucaryotic host cells. Eucaryotic host cells can be selected for example among yeast cells, such as *S. cervisiae*, filamentous fungi such as *Aspergillus* sp., insects cells such as S2 cells from *Drosophila* or Sf9 cells from *Spodoptera*, mammalian cells or plant cells.

Preferred eucaryotic host cells for mammalian protein synthesis are selected among mammalian host cell lines, especially, CHO, COS, HeLa, C127, 3T3, HepG2 or L (TK-) cell lines.

In another aspect of the invention, a cellular expression system comprises the culture of prokaryotic host cells. Preferred prokaryotic host cells include *Streptococci*, *Staphylococci*, *Streptomyces* and more preferably, *B. subtilis* or *E. coli* cells.

In a preferred embodiment, the method is characterized in that a host cell selected for the cellular expression system is a bacteria, preferably an *Escherichia coli* cell.

Host cells may be genetically modified for optimising recombinant RNA or protein synthesis. Genetic modifications that have been shown to be useful for in vivo expression of RNA or protein are those that eliminate endonuclease activity, and/or that eliminate protease activity, and/or that optimise the codon bias with respect to the amino acid sequence to synthesize, and/or that improve the solubility of proteins, or that prevent misfolding of proteins. These genetic modifications can be mutations or insertions of recombinant DNA in the chromosomal DNA or extra chromosomal recombinant DNA. For example, said genetically modified host cells may have additional genes, which encode specific transcription factors interacting with the promoter of the gene encoding the RNA or protein to synthesize.

Prior to introduction into a host cell, the DNA template is cloned in an expression vector. Such expression vectors include, among others, chromosomic vectors or episomal vectors or virus-derived vectors, especially, vectors derived from bacterial plasmids, phages, transposons, yeast plasmids and yeast chromosomes, viruses such as baculoviruses, papoviruses and SV40, adenoviruses, retroviruses and vectors derived from combinations thereof, in particular phagemids and cosmids.

For enabling secretion of translated proteins in the periplasmic space of gram bacteria or in the extracellular environment of cells, the expression vector may further comprise sequences encoding secretion signal appropriate for the expressed polypeptide.

The selection of the expression vector is guided by the type of host cells which is used for RNA or protein synthesis.

One preferred expression vector is a vector appropriate for expression in *E. coli*, and more particularly a plasmid containing at least one *E. coli* replication origin and a selection gene of resistance to an antibiotic, such as the $Ap^R$ (or bla) gene.

In one embodiment, the cellular concentration of α subunit of RNA polymerase is increased by overexpressing in the host cell, a gene encoding an α subunit of RNA polymerase.

Preferably, a gene encoding an α subunit of RNA polymera is a gene from *E. coli, T. maritima, T. thermotoga* or *T. neapolitana*.

For example, the host cell can comprise, integrated in the genome, an expression cassette comprising a gene encoding an α subunit of RNA polymerase under the control of an inducible or derepressible promoter, while the expression of the other subunits remains unchanged.

An expression cassette comprising a gene encoding an α subunit of RNA polymerase can also be cloned into the expression vector comprising the DNA template as mentioned above, or into a second expression vector.

For example, the expression cassette comprises the *E. coli* gene rpoA, under the control of a T7 phage promoter.

Thus, the invention also concerns a plasmid comprising:
(a) an expression cassette suitable for cloning into, a sequence encoding a protein of interest and synthesizing said protein into a host cell; and,
(b) an Open Reading Frame encoding α subunit of an RNA polymerase under the control of a promoter appropriate for expression in said host cell.

In a preferred embodiment, the concentration of α subunit in a cellular expression system is increased by induction of the expression of an additional copy of the gene encoding α subunit of RNA polymerase while expression of the other subunits remains unchanged.

In another specific and preferred embodiment of the method, said system enabling RNA or polypeptide synthesis from a DNA template is a cell-free system.

As used herein, a "cell-free system" or "cell-free synthesis system" refers to any system enabling the synthesis of a desired protein or of a desired RNA from a DNA template using cell-free extracts, namely cellular extracts which do not contain viable cells. Hence, it can refer either to in vitro transcription-translation or in vitro translation systems. Examples of eucaryotic in vitro translation methods are based on the extracts obtained from rabbit reticulocytes (Pelham and Jackson, 1976, *Eur. J. Biochem.*, 67: 247–256) or from wheat germ cells (Roberts and Paterson, 1973, *PNAS*, 70: 2330–2334). The *E. coli* S30 extract-based method described by Zubay, *Ann. Rev. Genet.* 7: 267 (1973) is an example of a widely used prokaryotic in vitro translation method.

For cell-free synthesis, the DNA template can be linear or circular, and generally includes the sequence of the Open Reading Frame corresponding to the RNA or protein of interest and sequences for transcription and translation initiation. Lesley et al., *J. Biol. Chem.* 2: 2632–2638 (1991) optimised the Zubay (1973) *E. coli* S30 based-method for use with PCR-produced fragments and other linear DNA templates by preparing a bacterial extract from a nuclease-deficient strain of *E coli*. Also, improvement of the method has been described by Kigawa et al., *FEBS Lett*, 442: 15–19 (1999) for semi-continuous cell-free production of proteins.

When a cell-free extract is used for carrying out the method of the invention, the concentration of α subunit of RNA polymerase is increased by adding purified α subunit of RNA polymerase to the cell free extract According to the method of the invention, it is understood that no other subunits of RNA polymerase are added to the cell-free extract, so that the stoechiometric ratio of α subunit/other subunits concentration is increased in the cell-free extract in favour to the α subunit. Preferably, said purified α subunit is added in a cell-free extract, more preferably a bacterial cell-free extract, to a final concentration comprised between 15 µg/ml and 200 µg/ml.

Purified α subunit of RNA polymerase can be obtained by the expression in cells of a gene encoding an α subunit of RNA polymerase and subsequent purification of the protein. For example, α subunit of RNA polymerase can be obtained by the expression of the rpoA gene fused in frame with a tag sequence in *E. coli* host cells, said fusion enabling convenient subsequent purification by chromatography affinity.

The term "cell-free extract" as used herein defines any reaction mixture comprising the components of transcription and/or translation machineries. Such components are sufficient for enabling transcription from a deoxyribonucleic acid to synthesize a specific ribonucleic acid, i.e mRNA synthesis. Optionally, the cell-free extract comprises components which further allow translation of the ribonucleic acid encoding a desired polypeptide, i.e polypeptide synthesis.

Typically, the components necessary for mRNA synthesis and/or protein synthesis in a bacterial cell-free extract include RNA polymerase holoenzyme, adenosine 5'triphosphate (ATP), cytosine 5'triphosphate (CTP), guanosine 5'triphosphate (GTP), uracyle 5'triphosphate (UTP), phosphoenolpyruvate folic acid, nicotinamide adenine dinucleotide phosphate, pyruvate kinase, adenosine, 3',5'-cyclic monophosphate (3',5'cAMP), transfer RNA, amino-acids, amino-acyl tRNA-synthetases, ribosomes, initiation factors, elongation factors and the like. The bacterial cell-free system may further include bacterial or phage RNA polymerase, 70S ribosomes, formyl-methionine synthetase and the like, and other factors necessary to recognize specific signals in the DNA template and in the corresponding mRNA synthesized from said DNA template.

A preferred cell-free extract is a bacterial cell-free extract, preferentially a bacterial cell-free extract from *E. coli* cells.

A preferred bacterial cell-free extract is obtained from genetically modified bacteria optimised for cell-free RNA and protein synthesis purposes. As an example, *E. coli* K12 A19 (as described in table 1) is a commonly used bacterial strain for cell-free protein synthesis.

The efficiency of the synthesis of proteins in a cell-free synthesis system is affected by nuclease and protease activities, by codon bias, by aberrant initiation and/or termination of translation. In an effort to decrease the influence of these limiting factors and to improve the performance of call-free synthesis, specific strains can be designed to prepare cell-free extract lacking these non-desirable properties.

It has been shown in the present invention that *E. coli* BL21Z which lacks Lon and OmpT major protease activities and is widely used for in vivo expression of genes, can also be used advantageously to mediate higher protein yields than those obtained with cell-free extracts from *E. coli* A19. Thus, one specific embodiment of the method of the invention comprises the use of cell-free extracts prepared from *E. coli* BL21Z.

In bacterial cell-free systems, a major part of the synthesized mRNA are unprotected against hydrolysis and can be subjected to degradation by the RNase E-containing degradosome present in bacterial cell-free extracts. Truncation mutations in the C-terminal or in the internal part of RNase E stabilise transcripts in *E. coli* cells. Thus, cell-free extracts from *E. coli* strains which are devoid of RNaseE activity and also protease activity, can be used in cell-free systems for RNA or protein synthesis. Such a strain, *E. coli* BL21 (DE3) Star, is commercially available from Invitrogen.

The RecBCD nuclease enzymatic complex is a DNA reparation system in *E. coli* and its activation depends upon the presence of Chi sites (5'GCTGGTGG3') on *E. coli* chromosome. Therefore, a recBCD mutation can be introduced in *E. coli* host cells in order to decrease the degradation of DNA templates in a cell-free system (Murphy, 1998).

When several codons code for the same amino acid, the frequency of use of each codon by the translatonal machinery is not identical. The frequency is increased in favor to preferred codons. Actually, the frequency of use of a codon is species-specific and is known as the codon bias. In particular, the *E. coli* codon bias causes depletion of the internal tRNA pools for AGA/AGG (argU) and AUA (ileY) codons. By comparing the distribution of synonymous codons in ORFs encoding a protein or RNA of interest and in the *E. coli* genome, tRNA genes corresponding to identified rare codons can be added to support expression of genes from various organisms. The *E. coli* BL21 Codon Plus-RIL strain, which contains additional tRNA genes modulating the *E. coli* codon bias in favor to rare codons for this organism, is commercially available from Stratagene and can be used for the preparation of cell-free extract.

Also, improved strains can be used to prevent aggregation of synthesized proteins which can occur in cell-free extracts. For example, it is well documented that chaperonines can improve protein solubility by preventing misfolding in microbial cytoplasm (Georgiou and Valax, 1996). In order to decrease a possible precipitation of proteins synthesized in a cell-free system, groES-gro-EL region can be cloned in a vector downstream an inducible or derepressible promoter and introduced into a *E. coli* host cell.

It has been found when carrying out the method of the invention, that both, protein yield and protein solubility, can further be improved in the presence of homologous or heterologous GroES/GroEL chaperonines in cell-free extracts, prepared from modified *E. coli* strains, whatever is the selected expression system.

In another embodiment, the cell-free extract is advantageously prepared from cells which overexpress a gene encoding α subunit of RNA polymerase.

Preferred host cells and plasmids used for overexpression of a gene encoding α subunits have been described previously.

Indeed, it is shown in the present invention that cell-free extracts prepared from cells overexpressing RNA polymerase α subunit provide improved yield of protein synthesis.

In a preferred embodiment, cell-free extracts are prepared from *E. coli* strains such as the derivatives of BL21 strain or the *E. coli* XA 4 strain, overexpressing the rpoA gene.

One advantage of the present embodiment is that the overexpression of α subunit of RNA polymerase is endogeneous and does not need the addition of an exogenous α subunit of RNA polymerase to the reaction mixture. It makes the experimental performance easier and decreases the total cost of in vitro protein synthesis.

In cell-free systems, linear DNA templates may affect the yield of RNA or protein synthesis and their homogeneity because of nuclease activity in the cell-free extract. By "protein homogeneity", it is meant that a major fraction of the synthesized product correspond to the complete translation of the Open Reading Frame, leading to full-length protein synthesis and only a minor fraction of the synthesized proteins corresponds to interrupted translation of the Open Reading Frame, leading to truncated forms of the protein. Thus, the desired protein synthesis is less contaminated by truncated polypeptides.

It is shown in the examples below that the use of elongated PCR-produced DNA template according to the method as defined above, improves the yield and the homogeneity of protein synthesis from cell-free systems.

Thus, in a preferred embodiment, the method of the invention comprises the use of PCR-produced DNA template further comprising an additional DNA fragment which is at least 3 bp long, preferably longer than 100 bp, and more preferably longer than 200 bp, located immediately downstream the stop codon of the Open Reading Frame encoding the desired RNA or protein of interest.

It has also been shown that the use of PCR-produced DNA template further comprising an additional DNA fragment containing transcriptional terminators, improves the yield and the homogeneity of the protein synthesis from cell-free systems.

One example of transcription terminators which can be used in the present invention is the T7 phage transcriptional terminator.

It is known in the art that adding purified RNA—polymerase may improve the yield of protein synthesis. For example, purified T7 polymerase can be added to the reaction mixture when carrying out cell-free synthesis using a T7 phage promoter. However, it is here shown that adding purified RNA thermostable polymerase, preferably *T. thermophilus*, in combination with the addition of purified α subunit of RNA polymerase and using bacterial promoter, enables much better yield than with the use of T7 polymerase promoter system.

Thus, in a preferred embodiment, purified thermostable RNA polymerase, preferably from *T. thermophilus*, is added into a bacterial cell-free extract The invention also provides an improved method for the production of a protein from a DNA template in a cell-free system characterized in that it comprises the steps of a) providing in a reaction mixture, a bacterial cell-free system enabling the coupling of in vitro transcription of a specific gene from a DNA template, and the corresponding protein synthesis;

b) adding to the reaction mixture the DNA template encoding the desired protein and purified α subunit of an RNA polymerase; and, c) optionally, adding a thermostable RNA polymerase, d) recovering the produced protein.

A preferred thermostable RNA polymerase which can be added in the reaction mixture in the above-defined method is from *T. thermophilus*, and is commercially available from Epicentre Technologies.

In another preferred embodiment of the method for the production of a protein from a DNA template, said purified α subunit is added to a final concentration comprised between 15 μg/ml and 200 μg/ml.

In another preferred embodiment, said DNA template comprises an amplification product of an Open Reading Frame encoding the desired protein to be produced. More preferably, said DNA template further comprises an additional DNA fragment, which is at least 3 bp long, preferably longer than 100 bp and more preferably longer than 200 bp, located immediately downstream the stop codon of said Open Reading Frame.

In another preferred embodiment, said DNA template further comprises an additional DNA fragment containing a transcriptional terminator. The transcriptional terminator is added downstream the desired gene-coding sequence.

An example of such transcriptional terminator is the T7 phage transcriptional terminator.

When using PCR amplification products as DNA template, providing a high yield and a homogeneity of protein synthesis, the method for the production of protein is particularly appropriate for serial synthesis of proteins in proteomic technologies, involving the parallel synthesis of a great number of proteins, for example, for the preparation of protein arrays.

It has also been shown in the present invention that the addition in the reaction mixture of a DNA-binding regulatory protein which binds to the promoter used in the cell-free expression system, improves the yield of protein synthesis. Accordingly, in one embodiment of the method of the invention, a DNA-binding regulatory protein is further added to the reaction mixture at step (b) of the method.

A DNA-binding regulatory protein is a protein which is not part of RNA polymerase holoenzyme but which binds specifically to a promoter region, said binding being correlated with the activation of transcription.

The invention also relates to the means for carrying out the methods of the invention.

Especially, the invention provides a genetically modified host cell characterized in that it comprises a recombinant DNA consisting of an Open Reading Frame encoding α subunit of an RNA polymerase under the control of a promoter appropriate for expression in said host cell. The introduction of a DNA template into said genetically modified host cell improves yield of RNA or protein synthesis.

In a preferred embodiment of the invention, a genetically modified host cell is a bacteria, preferably *E. coli* cell.

Since overexpression of a gene encoding α subunit of RNA polymerase may affect the general cellular protein synthesis and physiology of host cells, in a preferred embodiment, a promoter appropriate for the expression of an α subunit of RNA polymerase in the genetically modified host cell is an inducible or derepressible promoter. Using an inducible or derepressible promoter, it is thus possible to repress expression of the α subunit of RNA polymerase during cell growth and induce its expression together with the induction of the expression of the desired RNA or protein, when a sufficient amount of the microbial biomass has been yielded.

Examples of inducible or derepressible promoters include Plac, Ptac or PargC.

In a specific embodiment, a genetically modified host cell of the invention further comprises a heterologous gene encoding a protein of interest.

In the methods of the invention, the concentration of α subunit of RNA polymerase is modified in such a way that the ratio of α subunit/other subunits of RNA polymerase is increased, in favour to the α subunit in a cell-free system.

Accordingly, the invention also relates to a reaction mixture for cell-free protein synthesis characterized in that it comprises a bacterial cell-free extract and an amount of added purified α subunit of RNA polymerase.

In another embodiment, the reaction mixture for cell-free protein synthesis is characterized in that it is prepared from cells which overexpress the gene encoding α subunit of the RNA polymerase.

In a preferred embodiment, said purified or overexpressed α subunit of RNA polymerase at a final concentration comprised between 15 μg/ml and 200 μg/ml.

In another specific embodiment, the reaction mixture for cell-free synthesis is characterized in that it further comprises a DNA template with at least one UP element.

The invention also relates to the kit for carrying out the improved method of cell-free RNA and/or protein synthesis.

A kit for cell-free RNA and/or protein synthesis is characterized in that it comprises the following components:

a) a cell-free extract, preferably *E. coli* S30 cell-free extract, wherein said cell-free extract is obtained from cells overexpressing subunit of RNA polymerase;

b) optionally, appropriate buffers and compounds for carrying out in vitro transcription and/or translation reaction;

c) optionally, amino acid mixture lacking one amino acid.

In another embodiment, a kit for cell-free RNA and/or protein synthesis is characterized in that it comprises the following components:

a cell-free extract, preferably *E. coli* S30 cell-free extract;

purified α subunit of RNA polymerase;

optionally, appropriate buffers and compounds for carrying out in vitro transcription and/or translation reaction;

optionally, amino acid mixture lacking one amino acid.

Said purified or overexpressed α subunit provided in the kit of the invention is preferably purified from *E. coli* cells.

The invention further provides use of a purified α subunit of RNA polymerase for enhancing in vitro protein synthesis in a cell-free system. A preferred use is characterized in that said purified α subunit of RNA polymerase is added in a cell-free system at a concentration comprised between 15

μg/ml and 200 μg/ml. Another preferred use is characterized in that said purified α subunit of RNA polymerase is added in a cell-free system together with a thermostable RNA polymerase holoenzyme, preferably of *T. thermophilus*.

The one skilled in the Art will better appreciate the improvement of the methods of the invention for RNA and protein synthesis when reading the examples set forth below. Of course, the examples only illustrate certain preferred embodiments of the invention and should not be considered as limiting the scope of the claimed invention.

LEGENDS OF THE FIGURES

FIG. 1: A drawing showing SEQ ID NO: 17 and the transcriptional and translational initiation signals identified for the *B. stearothermophilus* argC gene.

An UP DNA element is shown in italic. −35 and −10 promoter sites as well as a Shine-Dalgarno site are underlined. Position of the oligonucleotide primers used for the PCR amplification of the 89-bp, 59-bp and 39-bp promoters are shown by arrow.

Figure 2:
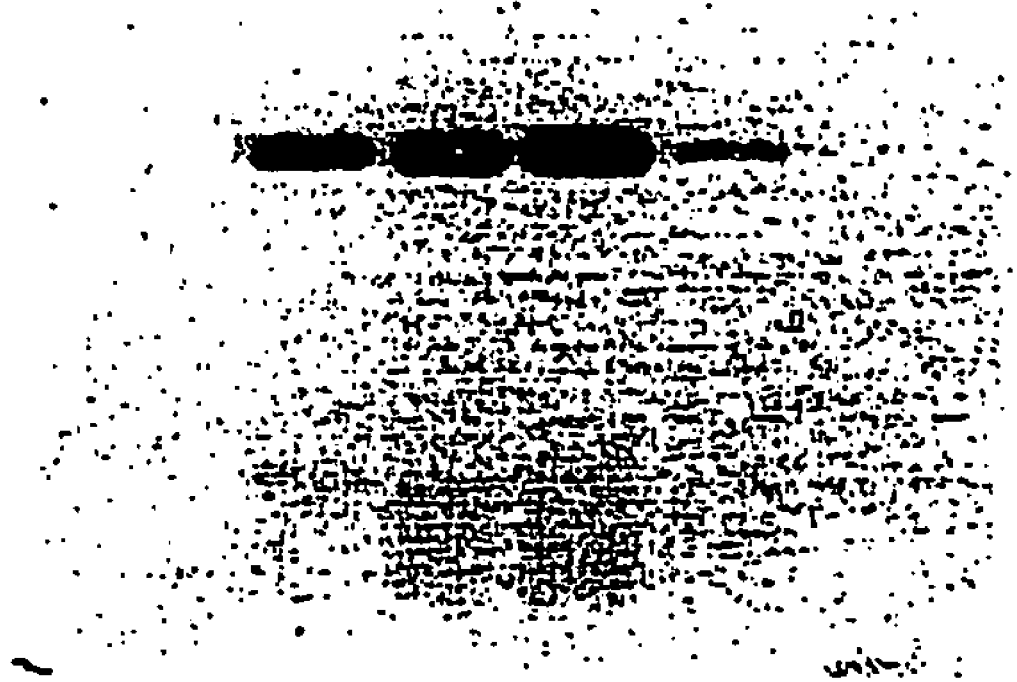

FIG. 2: SDS-PAGE showing the expression of the *B. stearothermophilus* argC gene using circular and linear DNA templates carrying the PargC promoter.

DNA templates used for synthesis:

Lane 1: plasmid pHAV2;
Lanes 2, 3, and 4: PCR-amplified DNA fragments carrying respectively 89-bp, 59-bp and 39-bp PargC promoter sequence.

Figure 3:
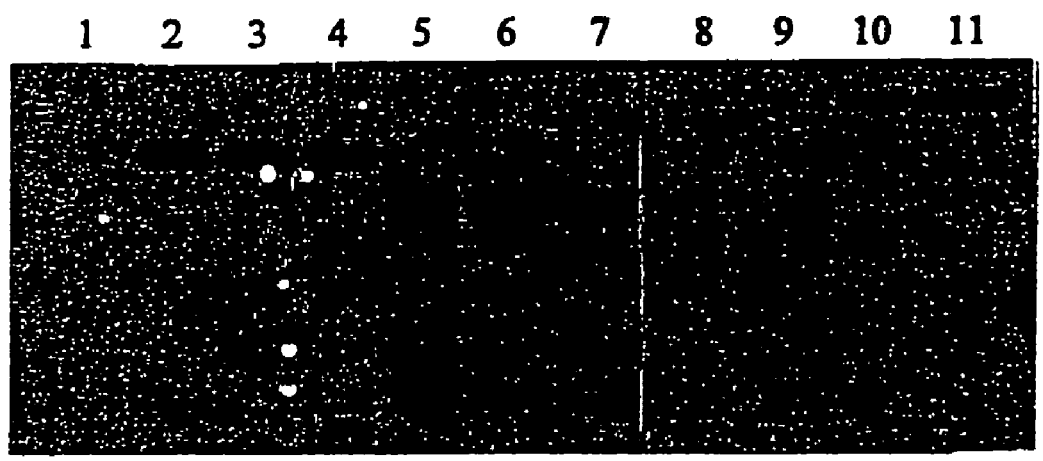

FIG. 3: SDS-PAGE protein profiles showing the cell-free synthesis of *B. stearothermophilus* ArgC and AmaA and *T. maritima* GntTm0439 proteins using different length linear DNA templates.

Lanes 1, 2, 3 and 4: ArgC synthesis, respectively without (control) and with +3 bp, +100 bp and +200 bp elongated sequence downstream the stop codon of the argC gene;
Lanes 5, 6 and 7: GntR synthesis, respectively without (control), with +3 bp and with +200 bp elongated sequence downstream the stop codon of the gnTm0349 gene;
Lanes 8, 9, 10 and 11: AmaA synthesis, respectively without (control), with +3 bp, +100 bp and +200 bp elongated sequence downstream the stop codon of the amaA gene.

Figure 4:
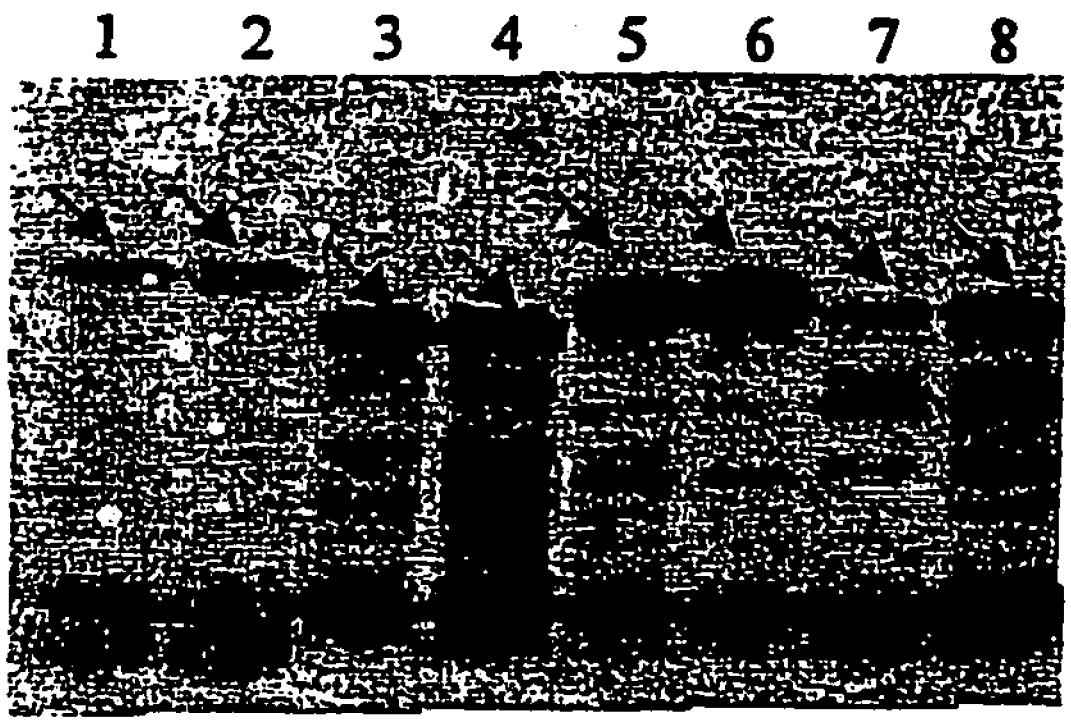

FIG. 4: SDS-PAGE showing the cell-free protein synthesis using extracts of isogenic strains *E. coli* B21 Star (DE3) (pRIL) and *E. coli* BL21 Star RecBCD (DE3) (pRIL).

A PCR product with a 200-bp downstream-elongated sequence was used as a DNA template.

Lanes 1, 3, 5 and 7: respectively, *B. stearothermophilus* AmaA and *T. maritima* LaclTm1856, XylTm1224 and GntR0275 proteins synthesized with *E. coli* BL21 Star (DE3) (pRIL) cell-free extract;
Lanes 2, 4, 6 and 8: the same proteins synthesized with *E. coli* BL21 Star RecBCD (DE3) (pRIL) cell-free extract. The corresponding protein band is shown by arrow.

Figure 5:
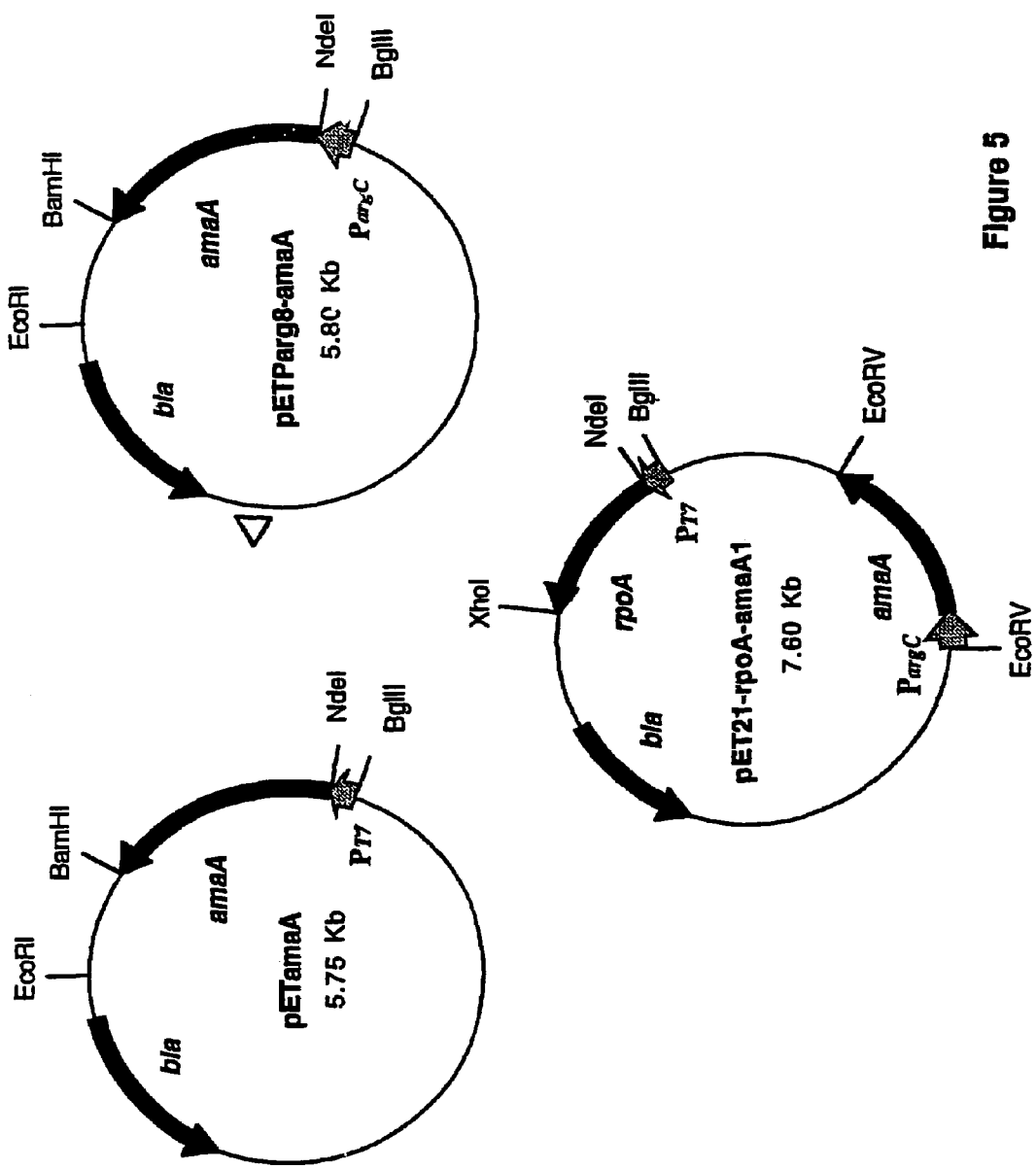

FIG. 5: Maps of plasmids pETamaA, pETarg8-amaA and pET21-rpoA-amaA1 carrying the *B. stearothermophilus* aminoacylase gene (amaA) as a model for in vitro and in vivo comparative studies.

Figure 6:
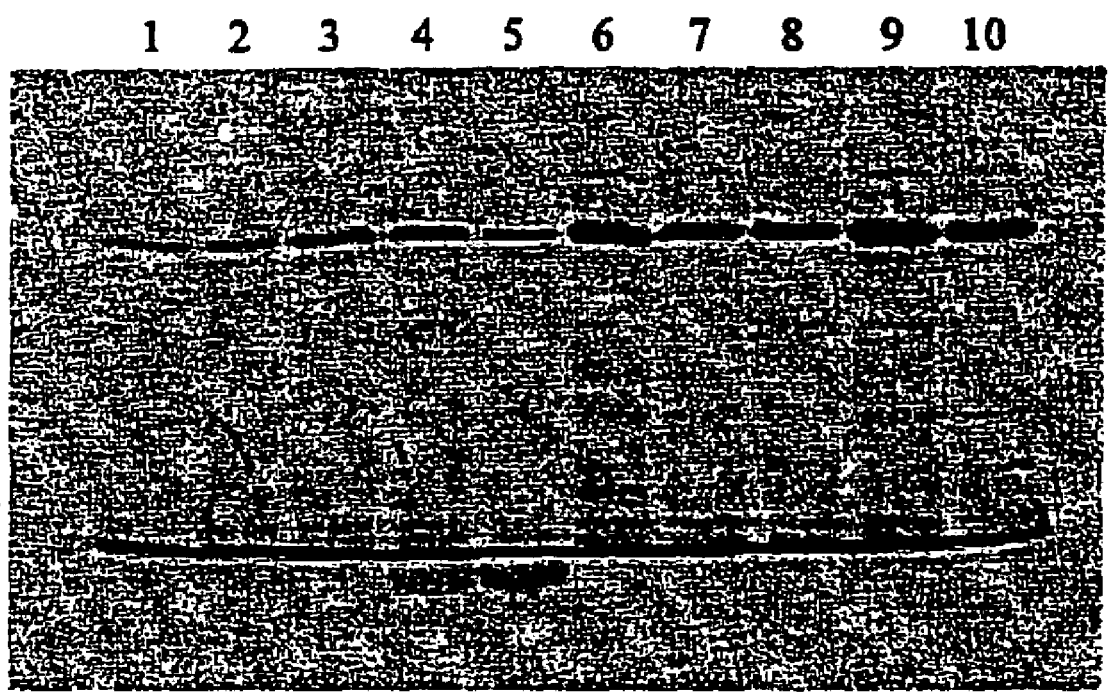

FIG. 6: SDS-PAGE showing aminoacylase production in a cell-free system without and with added exogenous RNA polymerase holoenzyme or α subunit of RNA polymerase.

Lane 1: synthesis without added exogenous factors;
Lane 2: synthesis with 3 μl of dialyzed *E. coli* RNA polymerase added;
Lane 3: synthesis with 3 μl of dialyzed *T. thermophilus* RNA polymerase added;

Lane 4: synthesis with 1 μl of dialyzed T7 RNA polymerase (Promega) added;
Lane 5: synthesis with 1 μl of dialyzed T7 RNA polymerase (laboratory sample) added;
Lanes 6, 7, 8 and 9: synthesis with 3 μl of α subunit of *E. coli* RNA polymerase added in combination with, respectively 3 μl of *T. thermophilus* RNA polymerase (lane 6), 3 μl of *E. coli* RNA polymerase (lane 7), 3 μl of dialyzed *E. coli* RNA polymerase (lane 8), 3 μl of dialyzed *T. thermophilus* RNA polymerase (lane 9);
Lane 10: synthesis with 3 μl of α subunit of *E. coli* RNA polymerase added.

Synthesis is carried out using pETParg8-amaA (lanes 1,2,3,6,7,8,9 and 10) or pET-amaA (lanes 4 and 5) plasmid DNA templates.

Other conditions are as specified in the Table 3 below.

Figure 7:
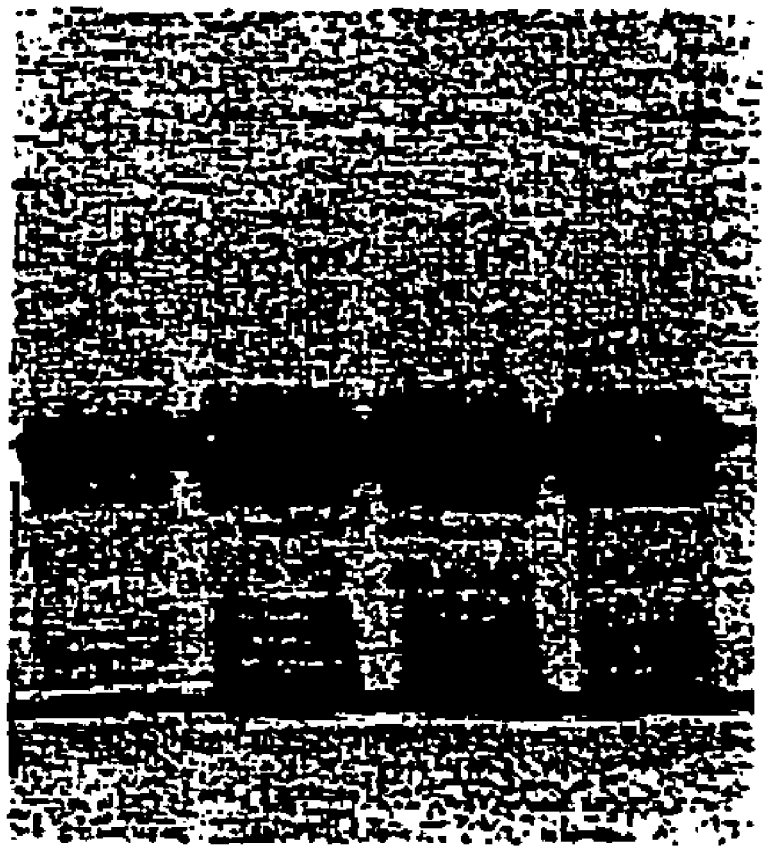

FIG. 7: SDS-PAGE showing GntTm0439 protein production in a cell-free system without and with exogenous α subunit of *E. coli* RNA polymerase or RNA polymerase holoenzyme using a linear DNA template.

A PCR-amplified DNA carrying the gntTm0439 gene of *T. maritima* DNA was added to a 30 μl reactional mixture with extracts of the *E. coli* BL21 Star RecBCD (DE3) (pRIL) strain Lane 1: synthesis without added exogenous factor;
Lanes 2, 3: synthesis with 3 μl of α subunit of *E. coli* RNA polymerase (final concentration 85 μg/ml) added, respectively without (lane 2) or with RNase A inhibitor (lane 3);
Lane 4: synthesis with 3 μl of dialyzed *T. thermophilus* RNA polymerase added.

Other conditions are as specified in Table 4.

Figure 8:
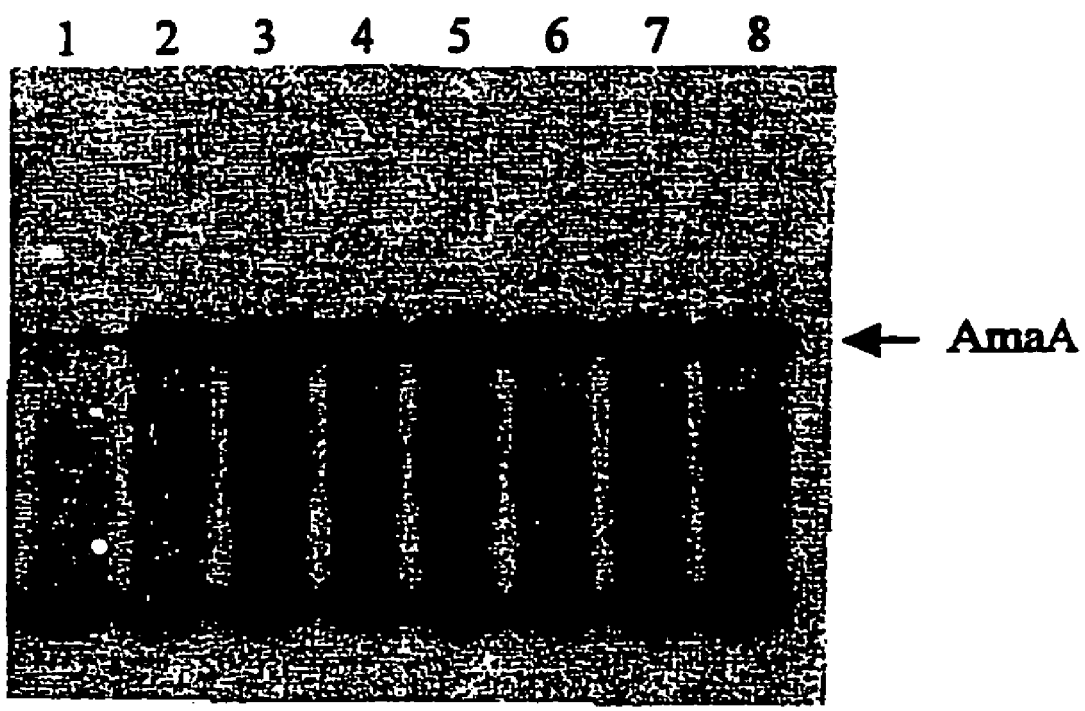

FIG. 8: SDS-PAGE showing optimization of cell-free aminoacylase synthesis by concomitant addition of the α subunit of *E. coli* RNA polymerase and *T. thermophilus* RNA polymerase holoenzyme.

Lane 1: synthesis with 5 μl of *T. thermophilus* RNA polymerase added;
Lanes 2 and 8: synthesis with 3 μl (lane 2) and 5 μl (lane 8) of α subunit of *E. coli* RNA polymerase added;
Lanes 3, 4, 5, 6 and 7: synthesis with respectively 3 μl, 1 μl, 2 μl, 3 μl and 4 μl of *T. thermophilus* RNA polymerase added respectively in combination with 3 μl, 4 μl, 3 μl, 2 μl and 1 μl of α subunit of *E. coli* RNA polymerase. Other conditions are as specified in Table 4 and Table 5 (see below).

Figure 9:
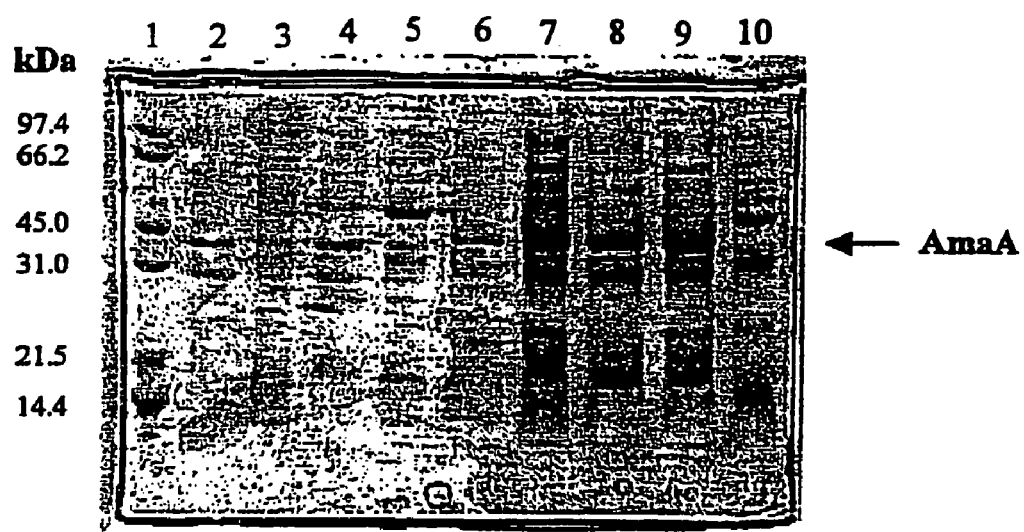

FIG. 9: Semi-continuous cell-free production of aminoacylase using semi-permeable membranes.

Lane 1: molecular markers;
Lanes 2 and 3: aminoacylase production in *E. coli* BL21 Star (DE3) (pET-amaA) IPTG-induced cells; lane 2 corresponds to the pellet fraction; lane 3 corresponds to the supernatant fraction.
Lanes 4 and 5: aminoacylase production in *E. coli* BL21 Star (DE3) (pETParg8-amaA) cells after the growth in a minimal M9 medium without arginine; lane 4 corresponds to the pellet fraction; lane 5 corresponds to the supernatant fraction.
Lanes 6 and 7: Cell-free synthesis of recombinant aminoacylas from pETParg8-amaA using cell-free extract of the *E. coli* BL21 Star RecBC (DE3) (pRIL) strain without (lanes 6) or with exogenous α subunit of *E. coli* RNA polymerase added (lanes 7);
Lanes 8 and 9: Cell-free synthesis of recombinant aminoacylase from a PCR-amplified DNA templates without (lane 8) or with exogenous α subunit of *E. coli* RNA polymerase added (lane 9).
Lane 10: the extract of *E. coli* BL21 Star (DE3) RecBC (pRIL) without synthesized aminoacylase.

Figure 10:
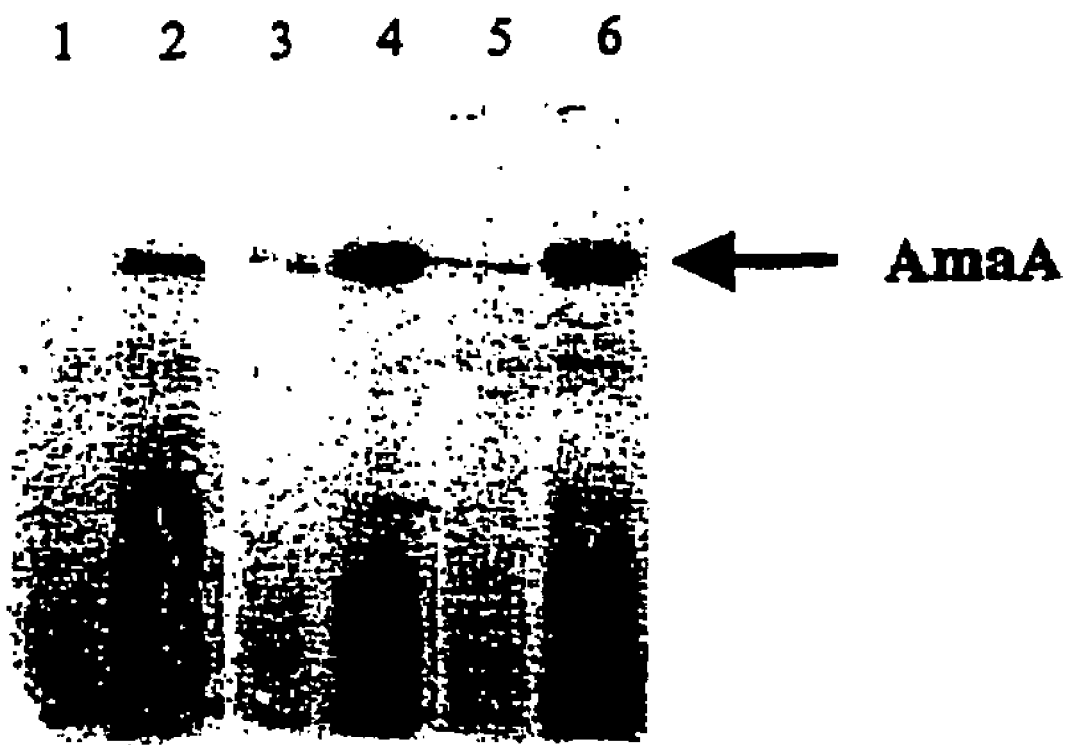

FIG. 10: SDS-PAGE showing the cell-free synthesis of aminoacylase in extracts of the *E. coli* BL21 Star (DE3)/pETrpoA$_{Ec}$ strain without (lanes 1, 3 and 5) and with IPTG induction (lanes 2, 4 and 6).

*E. coli* BL21 Star (DE3) cells carrying pET-rpoA$_{Ec}$ were grown without or with IPTG and their extracts were added to the reaction mixture at a final concentration of 1.6 mg/ml of a total protein. The *E. coli* RNA polymerase α subunit (Ec α) and the *E. coli* cAMP receptor protein (CRP) were dialyzed against buffer, as specified in Table 3 and added at a final concentration 100 μg/ml. Lanes 1 and 2 show synthesis without added exogenous proteins; lanes 3 and 4—with added α subunit; lanes 5 and 6—with added CRP. Reactions were carried out in the presence of RNase inhibitor.

Figure 11:
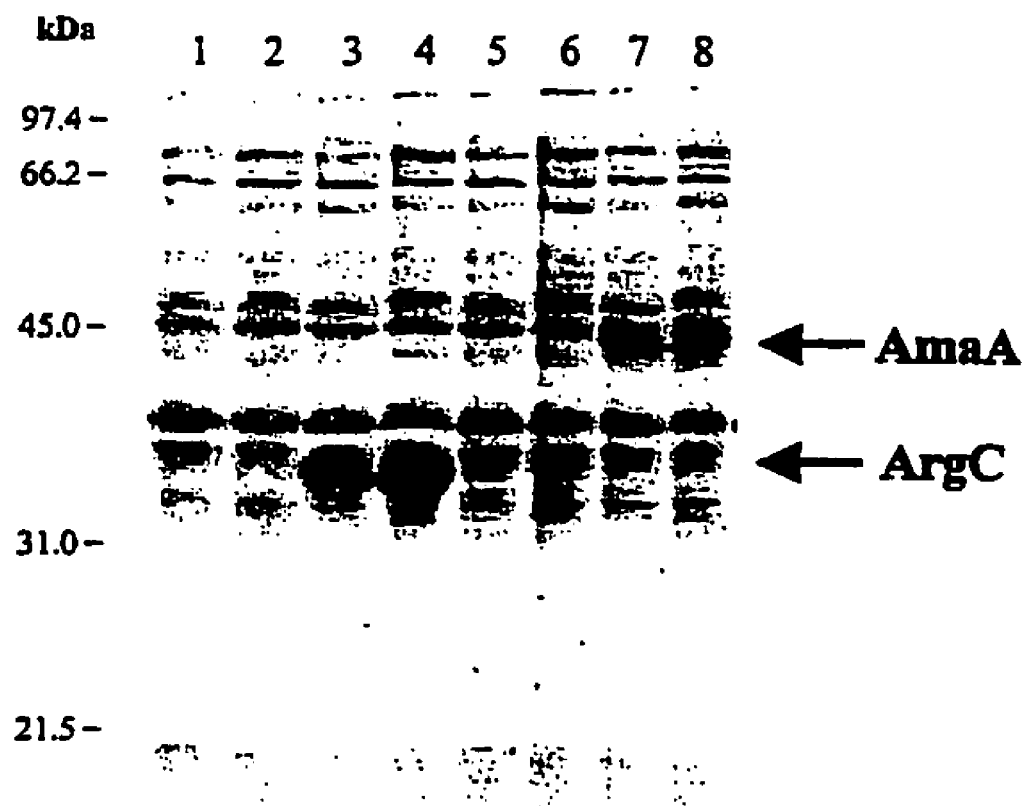

FIG. 11: SDS-PAGE showing in vivo expression of AmaA and ArgC genes in *E. coli* BL21 Star (DE3) cells grown with glucose or glycerol.

Extracts from cells which do not carry any plasmid (lanes 1 and 2) or carrying plasmids pHAV2 (lanes 3 and 4) or pBTacArgC (lanes 5 and 6) or pETPargAma (lanes 7 and 8). Cells were grown on M9 medium supplemented with 1% glucose (impair lanes) or with 1% glycerol (pair lanes). A supernatant of cell extracts containing 120 μg of a total protein was loaded on a polyacrylamid gel. Molecular mass references are indicated in kDa.

EXPERIMENTAL RESULTS

A. Materials and Methods

A.1 Bacterial Strains, Plasmids and Growth Conditions

Bacterial strains and plasmids used in the examples are described in Table 1.

*E. coli* strains were grown by vigorous shaking (180 rpm) at 28° C. or 37° C. on LB or M9 media (Miller, 1992) with appropriate antibiotics: ampicillin 100 μg/ml, chloramphenicol 25 μg/ml and kanamycin 25 μg/ml.

For preparation of cell-free extracts, *E. coli* cells were grown at 37° C. in a medium with 5.6 g/L KH$_2$PO$_4$, 28.9 g/L K$_2$HPO$_4$, 10 g/L yeast extract (Difco), 1 mM Mg-acetate, 10 g/L glucose, 15 μg/ml thiamine described by Zubay (Zubay, 1973). *B. stearothermophilus* cells were grown in LB broth (pH 7.3) at 56° C. with vigorous shaking.

For in viva expression of recombinant His-tagged proteins from a T7 promoter, recombinant *E coli* BL21 strains were grown in LB with 100 μg/ml ampicillin at 28° C. until an OD$_{600}$ 0.8–1.0. After induction by IPTG (1 mM), incubation was continued for 5 h. For in vivo expression of the recombinant *B. stearothermophilus* amaA gene from a PargC promoter, the corresponding *E. coli* BL21 recombinant strains were grown until ODB$_{600}$ 0.85. Then, cells were harvested by centrifugation, thoroughly washed three times with M9 medium and incubated overnight in a M9 medium. Cells were sonicated and used for SDS-PAGE analysis of proteins.

A.2 P1 Transduction recBCD nuclease-deficient strains of *E. coli* were constructed by P1 transduction as described previously (Miller, 1992). P1 vir lysate was obtained from *E. coli* strain KM21 as described previously (Murphy, 1998). P1 tranductants were selected on LB-plates supplemented with kanamycin. The introduction of a deleted recBCD DNA segment into a host chromosome was confirmed by direct PCR analysis of Km$^r$ Tc$^r$ cells using corresponding oligonucleotide primers.

TABLE 1

Bacterial strains and plasmids used in the exemples.

| Strain/plasmid | Relevant genotype/description | Reference/source |
| --- | --- | --- |
| *E. coli* K12 XA4 | F$^-$ argA nalA λ$^-$ λ$^s$ trpR hsdR | Laboratory collection |
| *E. coli* K12 KM21 | argE3 his-4 leuB6 proA2 thr-1 ara-14 galK2 lacY1 mtl-1 xyl-5 thi-1 rpsL31 tsx-33 supE Δ(recC ptr recB recD)::kan | Laboratory collection |
| *E. coli* K12 Top 10 | F' mcrA Δ(mrr-hsdRMS-mcrBC) φ80lacZΔM15 ΔlacX74 deoR recA1 araD139 Δ(ara-leu)7697 galU galK rpsL endA1 nupG | Invitrogen |
| *E. coli* K12 A19 | rna19 gdhA2 his-95 relA1 spoT1 metB1 | *E. coli* Genetic Stock Center |
| *E. coli* HMS174 (pAR1219) | F$^-$ hsdR19 recA1 rpoB331 IN(rrnD-rrnE)1 λ$^-$ pAR1219 (T7 gene 1 lacI) | ATCC |
| *E. coli* B BL21(DE3) | F$^-$ ompT hsdS$_B$ (r$_B^-$ m$_B^-$) gal (λclts857 ind1 Sam7 nin5 lac UV5-T7 gene 1) | Novagen |
| *E. coli* B BL21Z | F$^-$ ompT hsdS$_B$ (r$_B^-$ m$_B^-$) gal dcm Δ(lac-pro)::Tn10 | Laboratory collection |
| *E. coli* B BL21Star (DE3) | F$^-$ ompT hsdS$_B$ (r$_B^-$ m$_B^-$) gal dcm rne131 (DE3) | Invitrogen |
| *E. coli* B BL21-CodonPlus-RIL | F$^-$ ompT hsdS$_B$ (r$_B^-$ m$_B^-$) gal dcm$^+$Tet$^r$ endA Hte (argU ileY leuW Cam$^r$) | Stratagene |
| *E. coli* BL21 Star RecBCD (DE3) (pRIL) | F$^-$ ompT hsdS$_B$ (r$_B^-$ m$_B^-$) gal dcm$^+$Tet$^r$ endA Hte (argU ileY leuW Cam$^r$) recBCD (Km$^r$) | Laboratory construction |
| *T. neapolitana* DSM5068 | Wild type | Laboratory collection |
| *T. maritima* MSB8 | Wild type | Laboratory collection |
| *B. stearothermophilus* NCIB8224 | Wild type | Laboratory collection |
| pCR4-TOPO | bla kan, PCR cloning vector | Invitrogen |
| pHAV2 | pBTac2 vector carrying the *B. stearothermophilus* argC gene downstream PargC promoter | Savchenko et al., 1998 |
| pBTargC | pBTac2 vector carrying the *B. stearothermophilus* argC gene downstream Ptac promoter | Savchenko et al., 1998 |
| pET21d(+) | bla, T7 promoter expression vector | Novagen |
| pETamaA | pET3A vector carrying the *B. stearothermophilus* amaA gene downstream PT7 promoter | Dion et al., 1995 |
| pETParg8-amaA | pET3A vector carrying the *B. stearothermophilus* amaA gene downstream PargC promoter | Batisse, 1997 |

A.3 DNA Isolation

Bacterial biomass of *Thermotoga maritima* MSBB or *Bacillus stearothermophilus* NCIB8224 was harvested, washed with 10 mM Tris-HCl pH 8.0, 1 mM EDTA, 0.15 M NaCl solution and thoroughly resuspended in the same solution further containing 2 mg/ml of lysozyme. After an incubation for 20 min at 37° C., a lysis buffer (0.1 M Tris pH 8.0, 1% SDS) was added by gentle mixing and incubation was continued for 30 min at 60° C. The lysis was completed by adding proteinase K (0.6 mg/ml) and incubating the reaction mixture for 30 min at 60° C. After four consecutive extractions by phenol/chloroform/isoamylic alcohol (25:24:1, v/v), DNA was precipitated with 0.6 volume of isopropanol and centrifuged at 15000 rpm for 30 minutes at 4° C., rinsed with 70% ethanol and then resuspended in 10 mM Tris-HCl pH 8.0, 0.1 mM EDTA.

Plasmid DNA from *E. coli* cells was isolated according to Ausubel et al., (1993).

A.4 PCR Amplification and Construction of the DNA Templates

*B. stearothermophilus* PargCo promoter (Savchenko et al., 1998) was used for constructing the recombinant DNA templates to drive protein synthesis in a cell-free system.

Two oligonucleotide primers were used for amplification of the PargCo promoter-operator and corresponding to the upstream and downstream extremities of said promoter-operator (5'-CATAGACTTAGGGAGGGGC (SEQ ID NO: 1) and 5'-ATGATGATGATGATGATGCATATGTTC-CCCCTCACCCGTATG) (SEQ ID NO: 2); the latter contains 6 histidine codons to create a N-terminal tag.

Two other oligonucleotides, 5'-CCTCGAAAATTAT-TAAATATAC (SEQ ID NO: 3) and 5'-ACATTTGATTT-TATTTTTATAC (SEQ ID NO: 4), were also used to create upstream shortened fragments of promoter sequence, i.e., a 59-bp and a 39-bp fragment of the PargCo promoter-operator DNA (see also the FIG. 1). A DNA sequence coding for a protein of interest was amplified by PCR and fused to the *B. stearothermophilus* PargCo promoter by the overlap extension method (Ho et al., 1989).

Basically, the overlap extension method comprises the following steps:

at the first step, two separate DNA fragments corresponding to N-terminal and C-terminal parts of a given protein, were amplified from chromosomal DNA templates from *Bacillus stearothermophilus* NCIB 88224, *Escherichia coli* K12 XA4, *Thermotoga maritima* MSBB or *Thermotoga neapolitana* DSM 5068, with specific primers designed in such a way that the amplified products have overlapping sequences with the sequence downstream the PargC promoter region.

At a second step, the obtained PCR products were then combined in a subsequent fusion PCR product using only two flanking primers by annealing of the overlapped ends for providing the full-length recombinant DNA template.

All putative *T. maritima* genes were fused to a his-tag sequence in frame with the N-terminal extremity of the open reading frame to enable further purification of the protein by Ni-affinity chromatography.

Oligonucleotide primers used for amplification of putative ORFs from *T. maritima* genome are described in the Table 2 below.

TABLE 2

Oligonucleotide primers used for amplification of putative genes from *T. maritima*.

| Oligonucleotide primer | Putative protein* | Oligonucleotide sequence |
| --- | --- | --- |
| GntR-0439-His-N-term | GntTm0439 | 5'-ATGCATCATCATCATCATCATAAAAAAATCGAAGTGGACCTC (SEQ ID NO: 5) |
| Tm0439-GntR-down | -/- | 5'-GAACGAAACACCCTCCGCC (SEQ ID NO: 6) |
| GntR-0275-His-N-term | GntTm0275 | 5'-ATGCATCATCATCATCATCATATCGATGAAATAAAATCTGGAAAG (SEQ ID NO: 7) |
| TM-0275-GntR-down | -/- | 5'-CTCGCTGGAGGATCACAC (SEQ ID NO: 8) |
| Xyl-1224-His-N-term | XylTm1224 | 5'-ATGCATCATCATCATCATCATCCGAAATCGGTGAGAGCAG (SEQ ID NO: 9) |
| TM-1224-XylR-down | -/- | 5'-CTCCACGTGTAAATGTACAGTG (SEQ ID NO: 10) |
| LacI-1856-His-N-term | LacTm1856 | 5'-ATGCATCATCATCATCATCATCCAACAATAGAAGATGTCG (SEQ ID NO: 11) |
| TM-LacI-1856-down | -/- | 5'-GACCACTCGATCTGAACATCC (SEQ ID NO: 12) |

*Oligonucleotide primers were designed from *T. maritima* genome sequence (Nelson et al., 1999).

If necessary, PCR-produced templates were extracted from agarose gel, treated with phenol-chloroform-isoamyl (25:24:1, v/v), precipitated with ethanol and resuspended. Their DNA concentration was determined by spectrophotometry and confirmed by comparing band intensity with a Smart Ladder reference DNA (Eurogentec) after SDS-PAGE or agarose electrophoresis.

Otherwise, the quantified PCR-produced DNA templates were directly added to a cell-free extract to drive protein synthesis.

The E. coli XA4 rpoA gene coding for the α subunit of RNA polymerase was amplified by PCR using oligonucleotide primers 5'-GACA CCATGGAGGGTTCTGTGACAGAG (SEQ ID NO: 13) (the NcoI site is underlined) and 5'-CCG CTCGAGCTCGTCAGCGATGCTTGC (SEQ ID NO: 14) (the XhoI site is underlined). The E. coli XA4 crp gene coding for cAMP receptor protein (CRP) was amplified using oligonucleotide primers 5'-CATG CCATGGTGCTTGGCAAACC (SEQ ID NO: 15) and 5'-CCGCTCGAGACGAGTGCCGTAAACGAC (SEQ ID NO: 16). The amplified DNAs were cloned into pET21d(+) that allowed expression in frame to a His-tag sequence at the 5'-extremity of corresponding proteins.

Non-labelled and phosphorothioate-labeled oligonucleotide primers were purchased from Life Technologies.

A.5 Preparation of Cell-Free Extracts

E. coli strains were used for the preparation of cell-free extracts by toe method of Zubay (1973) with modifications as follow:

Cells were grown at 37° C., harvested in mid-log phase by centrifugation and washed twice thoroughly in ice-cold buffer containing 10 mM Tris-acetate pH 8.2, 14 mM Mg-acetate, 60 mM KCl, 6 mM β-mercaptoethanol.

Then, cells were resuspended in a buffer containing 10 mM Tris-acetate pH 8.2, 14 mM Mg-acetate, 60 mM KCl, 1 mM dithiotreitol and disrupted by French press (Carver, ICN) at 9 tonnes (≈20.000 psi). The disrupted cells were centrifuged at 30.000 g at 4° C. for 30 min, the pellet was discarded and the supernatant was centrifuged again. The clear lysate was added in a ratio 1:0.3 to the preincubation mixture containing 300 mM Tris-acetate at pH 8.2, 9.2 mM Mg-acetate, 26 mM ATP, 3.2 mM dithiotreitol, 3.2 mM L-amino acids, 3 U/ml pyruvate kinase (Sigma) and incubated at 37° C. for 80 min. The mixed extract solution was centrifuged at 6000 g at 4° C. for 10 min, dialysed against a buffer containing 10 mM Tris-acetate pH 8.2, 14 mM Mg-acetate, 60 mM K-acetate, 1 mM dithiotreitol at 4° C. for 45 min with 2 changes of buffer, concentrated 2–4 times by dialysis against the same buffer with 50% PEG-20.000, followed by additional dialysis without PEG for 1 hour. The obtained cell-free extract was aliquoted and stored at −80° C.

A.6 Cell-Free Protein Synthesis by Coupled Transcription-Translation Reaction

The expression system was based on the use of transcriptional and translational signals of the B. stearothermophilus argC gene (see FIG. 1). The argC gene is transcribed from a strong PargC promoter which overlaps a 42 bp argCo operator (Savchenko et al., 1996) recognized by the B. stearothermophilus ArgR repressor (Dion et al., 1997). However, the E. coli ArgR repressor has a very weak repression effect with respect to this operator. Therefore, heterologous genes can be overexpressed from B. stearothermophilus PargC promoter in E. coli cells (Savchenko et al., 1998).

The coupled transcription-translation reaction was carried out as described by Zubay (1973) with some modifications. The standard pre-mix contained 50 mM Tris-acetate pH 8.2, 46.2 mM K-acetate, 0.8 mM dithiotreitol, 33.7 mM NH4-acetate, 12.5 mM Mg-acetate, 125 µg/ml tRNA from E. coli (Sigma), 6 mM mixture of CTP, GTP and TTP, 5.5 mM ATP, 26.2 mM phosphoenol pyruvate, 8.7 mM CaCl2, 1.9% PEG-8000, 0.32 mM L-amino acids, 5.4 µg/ml folic acid, 5.4 µg/ml FAD, 10.8 µg/ml NADP, 5.4 µg/ml pyridoxin, 5.4 µg/ml para-aminobenzoic acid. When pyruvate was used as the energy regenerating compound (Kim and Swartz 1999), phosphoenol pyruvate was replaced in the standard reaction mixture by 32 mM pyruvate and 6.7 mM K-phosphate pH 7.5, 3.3 mM thiamine pyrophosphate, 0.3 mM FAD and 6 U/ml pyruvate oxidase (Sigma). Typically, 100–750 ng of circular plasmid DNA template or linear PCR-produced DNA template were added to 25 µl of a pre-mix containing all the amino acids except methionine, 10 µCi of [α$^{35}$S]-L-methionine (specific activity 1000 Ci/mmol, 37 TBq/mmol, Amersham-Pharmacia Biotech) and E. coli S30 cell-free extracts. The reaction mixture was then incubated at 370° for 90 min.

Semi-continuous synthesis using PargC-mediated cell-free system was performed as described by Kigawa et al. (Kigawa et al., 1999) with modifications as follow:

The standard reaction mixture contains 55 mM HEPES KOH pH 7.5, 1.7 mM DTT, 1.2 mM ATP, 0.8 mM of each CTP, GTP and UTP, 0.64 mM cAMP, 68 mM folinic acid, 180 mg/ml E. coli t-RNA, 210 mM K-glutamate, 27.5 mM ammonium-acetate, 10.7 mM Mg-acetate, 80 mM creatine phosphate, 250 µg/ml creatine kinase from rabbit muscle (Roche), 0.67 U/µl RNase A inhibitor (Takara), 4% PEG 8000, 1 mM L-amino acid mixture and cell extracts of the E. coli BL21 Star RecBC (DE3) (pRIL) strain. Circular plasmid or linear PCR-produced DNA template was used as a template at a concentration of 10 µg/ml. If necessary, α subunit of E. coli RNA polymerase (final concentration 153 µg/ml) was added to the reaction mixture. Typically, 150 µl of a reaction mixture was placed in dialysis membrane (Cellulose ester irradiated membrane, MWCO 25000, Spectrum, purchased from Interchim) and incubated in 3 ml of the same reaction mixture solution but devoid of RNase inhibitor, S30 extract, creatine kinase and DNA at 37° C. for overnight. 10 µl of samples were taken, precipitated with acetone and analyzed by SDS-SPAGE, followed by coloration with Coomassie Brilliant Blue (Sigma).

RNA polymerase of E. coli or Thermus thermophilus were purchased from Epicentre Technologies. RNA polymerase of bacteriophage T7 was purchased from Promega or purified from E. coli BL21 (pAR1219) strain (purchased from ATCC) as described by Zawadski and Gross (1991). The enzymes were added to the cell-free extracts at the conditions and concentrations described below. One unit of RNA polymerase holoenzyme catalyzes the incorporation of one nmol of a radiolabeled ribonucleoside triphosphate into RNA in 10 min at 37° C. for E. coli holoenzyme or in 60 min at 65° C. for T. thermophilus holoenzyme (Epicentre Technologies), whereas one unit of T7 RNA polymerase catalyzes the incorporation of 5 nmol rCTP into acid-soluble product in 60 min at 37° C. (Promega).

If necessary, the protein samples were treated at 80° C. for 10 min and then quickly centrifuged. The supernatant was precipitated with acetone and used for protein separation on SDS-PAGE. After coloration with Coomassie Brilliant Blue, gels were treated with an amplifier solution (Amersham-Pharmacia Biotech), fixed on a 3 MM paper by vacuum drying and the radioactive bands were visualized by autoradiography using BioMax MR film (Kodak). Molecular weights of putative proteins were deduced from ORFs of the T. maritima genome and further confirmed by migration of the corresponding proteins on SDS-PAGE. Quantification of cell-free synthesized proteins (as monomer equivalent) was performed either, (i), by comparing non-radiolabeled protein bands with known reference proteins after coloration with EZBlue gel staining reagent (Sigma) or, (ii), by counting radioactivity of $^{35}$S-labeled protein bands with Phosphormager 445SI (Molecular Dynamics).

A.7 Purification of His-Tagged Proteins

Recombinant bacteria were suspended in a buffer (50 mM NaH$_2$PO$_4$, pH 8.0, 300 mM NaCl, 10 mM imidazole), broaken by sonication and His-tagged proteins were purified by affinity chromatography on a Ni-NTA column (Qiagen). The column was washed successively with 10×bed volumes of the mentioned buffer and proteins were eluted by 6×bed volumes of elution buffer [50 mM Tris-HCl pH 7.9, 50 or 300 mM NaCl, 200 or 400 mM imidazole, 5% (vol/vol) glycerol)] and then dialysed against buffer containing 20 mM NaH$_2$PO$_4$, pH 8.0, 5 mM β-mercaptoethanol, 5% (vol/vol) glycerol. Protein concentration was measured by Bradford method (Bradford, 1976).

Proteins synthesized by cell-free synthesis were purified using Ni-NTA-magnetic agarose beads (Quiagen).

B. EXAMPLES

B.1 UP Element Increases the Strength of a PargC in a Cell-Free System.

It has been shown previously that a PargC promoter of the argCJBD operon of *B. stearothermophilus* NCIB8224 strain is able to mediate a high gene expression in *E. coli* host cells (Sakanyan et al., 1990; Savchenko et al., 1998). It was postulated, that this surprising strength for a amino acid biosynthetic promoter could be related with the presence of a 19-nt AT-rich sequence located upstream a −35 promoter site (see FIG. 1).

In order to check if the presence of a UP-like sequence on promoter could improve protein synthesis in a cell-free system, plasmid pHAV2 (Savchenko et al., 1998) enabling PargC-mediated expression of the *B. stearothermophilus* argC gene, was added to a cell-free system at a final concentration of 5 μg/ml and a coupled transcription-translation Was performed at 37° C. for 90 min. The reaction mixture was heat-treated at 65° C. for 30 min and precipitated by centrifugation. The pellet was discarded and ArgC protein synthesis was evaluated by autoradiography. As shown in FIG. 2, lane 1, [$^{35}$S]methionine incorporation into the ArgC protein synthesized from pHAV2 was 3fold higher than incorporation into the ArgC protein synthesized from a pBTargC DNA template (Savchenko et al., 1998). In the latter, argC transcription is promoted from a Ptac promoter known as a strong one (De Boer et al, 1983). These results demonstrate that the *B. stearothermophilus* PargC promoter can be used for high gene expression, especially for cell-free protein synthesis.

In order to estimate the exact effect of the UP-like sequence on the PargC promoter strength, three PCR-amplified DNA fragments were generated consisting respectively of a 89-bp length natural promoter region or of its shortened 59-bp fragment which still carries the 19-bp AT-rich sequence (UP element), or of a 39-bp long fragment in which the 19-bp AT-rich sequence was eliminated (see FIG. 1). Equimolar quantities of non-purified PCR-produced DNA templates were added to the cell-free extracts prepared from *E. coli* BL21Z and cell-free protein synthesis was carried out at the conditions described above.

The results in FIG. 2 show that the 89-bp-long PargC promoter and the 59-bp long promoter mediated a high synthesis of ArgC protein. On the contrary, a dramatic diminution of ArgC protein synthesis was detected from the 39-bp long promoter lacking the UP element Quantitative comparison of $^{35}$S-labelled proteins indicated that ArgC expression mediated from the 39-bp long promoter region was nearly 22-fold weaker than expression from the 59-bp long promoter region.

These data showed that the *B. stearothermophilus* PargC promoter behaves as a strong promoter in *E. coli* cell-free system and that the UP-element determines this high promoter strength.

B.2 Elongated PCR Products Provide Better Yield of RNA or Protein Synthesis in a Cell-Free Synthesis System Large variations between the quantities of different synthesized proteins are not suitable for parallel synthesis of numerous proteins for proteomic technology applications such as preparation of protein arrays.

The treatment of PCR amplified DNA fragments with T4 ligase improved somehow the synthesis of some model proteins. It has been proposed that circular DNA molecules, in contrast to linear molecules, lack free extremities subjected to exonuclease degradation. Thus, DNA ligation provides a mean to obtain reproducible yield of protein synthesis in cell-free systems. However, DNA ligation requires the introduction of an additional step which can not be desired for rapid and parallel synthesis of proteins at a large scale.

In order to improve the yield and the homogeneity of any synthesized protein using a linear DNA template, another approach which consists of protecting DNA fragment with phosphorothioate, was tested (Spitzer and Eckstein, 1988). DNAs were labelled with phosphorothioate at the 5'-end of one or both oligonucleotide primers used for the second step of the overlap extension method (see Materials and Methods) to provide protected DNA template. The amplified DNA fragments were purified and used at equimolar quantities as linear DNA template for cell-free protein synthesis. It was found that protection of one or both ends increased *T. maritima* LacITm1856 or *B. stearothermophilus* ArgC proteins synthesis nearly 2-fold. However, the use of phosphorothioate-labeled primers provoked the appearance of background PCR products which are not desirable. This means that each phosphorothioate-labeled primer pair would need to be tested by a preliminary PCR in order to choose optimal amplification conditions. Taking into consideration this disadvantage and a high price of phosphorothioate-labeled primers, this could then not be appropriate for a convenient serial synthesis of proteins.

For cell-free protein synthesis, the commonly used linear DNA template consists of a promoter linked to the ORF sequence ending at the stop codon. In the method of the invention, it is proposed to use elongated PCR-amplified DNA template in the direction downstream the stop codon. Elongated PCR-produced DNA templates of different lengths were prepared for three model genes: the argC and ameA genes from *B. stearothermophilus* (Sakanyan et al., 1990; 1993a; 1993b) and the gntTm0439 gene from *T. maritima* coding for a putative regulator (Nelsson et al., 1999). Each corresponding gene sequence has been linked to the above-mentioned 89-bp PargC promoter region. The PCR-produced DNA templates were elongated by 3 bp, 100 bp and 200 bp of extra genomic sequences downstream the stop codon of each gene.

As shown in FIG. 3, ArgC and AmaA proteins synthesis in cell-free extract from *E. coli* BL21Z are significantly increased by the elongation of their coding sequences with extra-genomic sequences. Especially, as it can be visualized in lanes 10 and 12 of FIG. 3, a drastic improvement was observed for the amaA gene expression. It appears that protein synthesis increases as a function of the length of the extra-genomic sequence added downstream the amaA gene. The GntTm0439 protein was found to be highly synthesized from a short DNA template carrying the only coding region, showing that the effect of extra-DNA sequence was less pronounced for this model gene. The improvement of bacterial protein yield could be explained by the formation of secondary structures downstream the coding region which protect 3'-extremity of mRNA against ribonuclease digestion and degradation of the coding region. Therefore, the absence of degraded mRNAs increases the yield of homogenous protein and decreases the appearance of truncated proteins.

Transcriptional terminators form secondary structures at the 3'-extremity of mRNA which can protect it against RNA exonucleases and thereby increase a protein yield in bacterial cells (Ehretsmann et al., 1992). To assess the influence of terminator signals on in vitro protein synthesis the B. stearothermophilus amaA gene was amplified on a plasmid pETParg8-amaA (FIG. 5; Batisse, 1997) enabling the addition downstream the amaA stop codon of a 48 bp DNA fragment, containing a T7 phage transcriptional terminator. Such a DNA provided a higher protein yield in extracts of E. coli BL21 Star RecBCD (DE3) (pRIL) cells which is comparable to the yield which was obtained with an elongated 200 bp DNA prepared from the B. stearothermophilus NCIB8224 genome.

A gene-downstream elongation also appeared to delay DNA exonucleasic degradation in cell-free extracts prepared from E. coli BL21 Star (DE3) (pRIL) cells. However, in order to decrease DNase activity, recBCD mutation was introduced in this strain by P1 transduction (see Materials and Methods). Then, a 200-bp downstream-elongated DNA template was amplified for four different genes and used as a template in cell-free protein synthesis using cell-free extracts of isogenic strains E. coli B21 (DE3) Star (pRIL) and its RecBCD derivative. As shown in FIG. 4, the yield of all proteins, namely AmaA of B. stearothermophilus, and three others, LaclTm1856, XylTm1224 and GntRTm0275 of T. maritima was nearly 1.5–2 times better in the recBCD mutant environment than in the parent strain cell-free extracts.

These data revealed that the use of elongated DNA templates can improve significantly the yield and the homogeneity of protein synthesis.

Further recombinant DNA molecules for cell-free protein synthesis were constructed by adding a N-terminal His tag, but not a C-terminal tag to the coding sequence of analysed genes. The higher yield of various proteins in a cell-free system provided by the elongated sequences enables to apply a metal-affinity chromatography for protein purification at a small scale. This would not have been possible with lower yield of proteins.

Affinity purification is also essential to decrease the presence of truncated proteins in samples caused by aberrant translation in cell-free synthesis systems.

Thus, the elongation of a PCR-amplified DNA provides much higher and homogenous production of different proteins. The validity of this improvement was also proven in combination with the other improvements of the methods of the invention.

As a result, this improvement enables to provide new methods of protein synthesis suitable with a simple and rapid purification of proteins.

B.3. Thermostable RNA Polymerase Increases the Yield of Cell-Free Protein Synthesis.

Cell-free extracts from E. coli cells have sufficient amounts of endogenous RNA polymerase to assure a high gene expression. However, K is known that adding purified polymerase can yet improve the expression level.

As shown in FIG. 5, a recombinant plasmid was constructed by cloning the B. stearothermophilus amaA gene downstream the PargC promoter in the pET3A vector (Batisse, 1997). The resulted pPargC8-amaA plasmid was purified, treated by phenol-chloroform-isoamyl to eliminate traces of RNase and precipitated by ethanol. Plasmid DNA (final concentration of 25 μg/ml) was added to cell-free extracts from the E. coli BL21 Star RecBCD (DE3) (pRIL) strain and the reaction of protein synthesis was performed at 37° C. for 2 h in the presence or in the absence of exogenous RNA polymerase. E. coli holoenzyme and T. thermophilus holoenzyme were compared for their ability to drive protein synthesis. Both commercial enzyme samples were found to inhibit gradually protein synthesis at concentrations varying from 0.04 to 024 U/ml of E. coli holoenzyme or from 0.1 to 0.6 U/ml of T. thermophilus holoenzyme. In order to ensure that protein synthesis is not inhibited by the presence of glycerol from holoenzyme samples, enzymes were shortly dialyzed against the buffer used for cell-free synthesis and then added to the cell-free reaction mixture. As shown in FIG. 6 and table 3, it was found that the addition of the dialysed T. thermophilus thermostable RNA polymerase (at 0.3 U/ml) increased cell-free aminoacylase production nearly 5-fold. It is to be noticed that no improvement of protein synthesis was detected by adding the dialysed E. coli RNA polymerase holoenzyme alone. Thus, the results surprisingly show that adding heterologous thermostable RNA polymerase in E. coli cell-free extracts drastically increases cell-free protein synthesis from the PargC promoter.

B.4. Addition of α Subunit of E. coli RNA Polymerase Drastically Increases Protein Production in Cell-Free Expression System The role of the α subunit of RNA polymerase, when associated with other subunits to form the polymerase holoenzyme, is well established for mRNA synthesis in bacterial cells (Ebright and Busby, 1995). Unexpectedly, it has been found that increasing the concentration of α subunit, independently of other subunits concentration, is sufficient to drastically increase aminoacylase synthesis using the PargC promoter. Indeed, a pure His-tagged α subunit of E. coli RNA polymerase at a final concentration of 0.1 mg/ml increased aminoacylase production nearly 13-fold, as shown in FIG. 6 and table 3. Moreover, a two-fold increase of protein synthesis has been detected when adding purified α subunit of RNA polymerase as compared, for example, to adding thermostable T. thermophilus RNA polymerase.

TABLE 3

Effect of xogenous T. thermophiius, E. coli RNA and T7 polymerase holoenzymes as well as the E. coli RNA polymerase α subunit on cell-free synthesis of aminoacylase*.

| N° | Added compound** | Efficiency of synthesis, % |
|---|---|---|
| 1 | without | 4.4 |
| 2 | Ec RNP (dialyzed) 3 μl*** | 3.7 |
| 3 | Tt RNP (dialyzed) 3 μl*** | 20.8 |
| 4 | T7 RNP (Promega) 1 μl (15 U) | 22.2 |
| 5 | T7 RNP (laboratory sample) 1 μl (14 mg/ml) | 8.8 |
| 6 | Ec α 3 μl + Tt RNP 3 μl | 64.8 |
| 7 | Ec α 3 μl + Ec RNP 3 μl | 41.2 |

TABLE 3-continued

Effect of xogenous *T. thermophiius*, *E. coli* RNA and T7 polymerase holoenzymes as well as the *E. coli* RNA polymerase α subunit on cell-free synthesis of aminoacylase*.

| N° | Added compound** | Efficiency of synthesis, % |
|---|---|---|
| 8 | Ec α 3 μl + Ec RNP (dialyzed) 3 μl*** | 59.4 |
| 9 | Ec α 3 μl + Tt RNP (dialyzed) 3 μl*** | 100% |
| 10 | Ec α 3 μl | 58.4 |

*The plasmids pPargC8-amaA and pET8-amaA were added at equimolar concentrations (approxim. 25 μg/ml) to the extracts of *E. coli* BL21 Star RecBCD (DE3) (pRIL) to direct aminoacylase synthesis from PargC (N° 1, 2, 5, 6, 7, 8, 9, 10) or T7 promoters (N° 4 and 5), respectively.
**Added RNA polymerase holoenzymes were of T7 bacteriophage—T7, *E. coli*—Ec and *T. thermophilus*—Tt.
***RNA polymerase samples were dialyzed against a buffer 250 mM NaCl, 50 mM Tris-HCl pH 7.5, 1 mM DTT, for 30 min at 4° C.

Thus, surprisingly, it appears that gene overexpression can take place by added only α subunit of RNA polymerase to cell-free system rather than the active holoenzyme.

The effects of both *T. thermophilus* RNA polymerase and α subunit of *E. coli* RNA polymerase on cell-free protein synthesis were also tested using linear PCR-produced DNA templates for the putative gntTm0439 gene of *T. maritima* which already provided a rather high yield of protein without elongation of its downstream sequence. However, as shown in FIG. 7, a clear positive effect was detected by the addition of *T. thermophilus* RNA polymerase or, especially, the α subunit of *E. coli* RNA polymerase to the reaction mixture. Quantification of the incorporated $^{35}$S-methionine indicated that the addition of *T. thermophilus* RNA polymerase or the single α subunit of *E. coli* RNA polymerase, respectively provided 1.7 and 2-fold higher yield of GntTm0439 synthesis, as shown in Table 4. The presence of RNase A inhibitor with α subunit did not influence the yield of the protein. However, it was noticed, that the presence of RNase A inhibitor can improve the production of some other proteins from a linear DNA template when α subunit was also added.

TABLE 4

Effect of *T. thermophilus* RNA polymerase and α subunit of *E. coli* RNA polymerase on cell-free synthesis of a GntTm0439 *T. maritima* from a linear DNA template.

| N° | Addition of *T. thermophilus* RNP and α subunit of *E. coli* RNP* | Efficiency of synthesis, %** |
|---|---|---|
| 1 | — | 46 |
| 2 | Ec α 3 μl | 98.3 |
| 3 | Ec α 3 μl + 0.5 μl RNase A inhibitor | 100 |
| 4 | Tt RNP 3 μl | 82 |

***T. thermophilus* RNA polymerase holoenzyme (Tt RNP) and *E. coli* RNA polymerase α subunit (Ec α) were dialyzed against buffer, as specified in Table 3.

It is possible that RNA polymerase undergoes to dissociation in cell-free extracts and its association into the holoenzyme molecule is enhanced by adding exogenous α subunit Alternatively, α subunit appears to recognize and bind the UP-element, thereby accelerating the formation of a functional RNA polymerase-DNA complex Irrespective of the nature of the observed phenomenon, this data is indicative that a transcriptional machinery potency is still essential for improving mRNA or protein synthesis in cell-free system.

B.5. Addition of Exogenous α Subunit and RNA Polymerase Holoenzyme have Synergic Effect in Cell-Free Expression Systems Next, it has been evaluated whether α subunit of *E. coli* RNA polymerase and *T. thermophilus* RNA polymerase holoenzyme could provide together a stimulating effect on protein synthesis. A pPargC8-amaA plasmid DNA was used as a template and protein synthesis was initiated by adding different concentrations of purified α subunit of *E. coli* RNA polymerase and thermostable RNA polymerase holoenzyme to a cell-free extract from the *E. coli* BL21 Star ReBCD (DE3) (pRIL) strain. As shown in FIG. 8 and Table 5, the addition of both compounds provided higher aminoacylase synthesis than addition of each of them separately. When adding 2 μl of 0.3 U/ml of *T. thermophilus* RNA polymerase and 3 μl of 0.1 mg/ml of α subunit (corresponding to 0.3 U/ml: 0.1 mg/ml), the highest aminoacylase synthesis level was observed. Synthesis level increased 18-fold and 2-fold in comparison with the addition of only *T. thermophilus* RNA polymerase or *E. coli* RNA polymerase α subunit, respectively. Also, aminoacylase synthesis was slightly improved when α subunit was added with *E. coli* RNA polymerase holoenzyme to cell-free extract (see Table 3).

TABLE 5

Synergic effect of *T. thermophilus* RNA polymerase holoenzyme and α subunit of *E. coli* RNA polymerase on cell-free synthesis of *B. stearothermophilus* aminoacylase

| N° | Addition of *T. thermophilus* RNP and α subunit of *E. coli* RNP* | Efficiency of synthesis, %** |
|---|---|---|
| 1 | Tt RNP 5 μl | 2.9 |
| 2 | Ec α 3 μl | 47.3 |
| 3 | Tt RNP 3 μl + Ec α 3 μl | 98.6 |
| 4 | Tt RNP 1 μl + Ec α 4 μl | 64.4 |
| 5 | Tt RNP 2 μl + Ec α 3 μl | 100 |
| 6 | Tt RNP 3 μl + Ec α 2 μl | 86.8 |
| 7 | Tt RNP 4 μl + Ec α 1 μl | 59.2 |
| 8 | Ec α 5 μl | 33.2 |

*Specific activity of *T. thermophilus* RNA polymerase holoenzyme was 2.5 u/μl; initial concentration of α subunit of *E. coli* RNA polymerase was 0.85 mg/ml.
**The highest efficiency of aminoacylase synthesis is taken as 100%.

Thus, these data revealed that the addition of exogenous α subunit of bacterial RNA polymerase and the RNA polymerase holoenzyme have synergic effect on the PargC-mediated cell-free protein synthesis. A positive effect of α subunit is observed in combination with any used exogenous RNA polymerase holoenzyme. However, the efficiency of cell-free protein production is significantly improved by adding together the α subunit of *E. coli* RNA polymerase and *T. thermophilus* RNA polymerase holoenzyme to the reaction mixture.

B.6. PargC-Mediated Cell-Free Protein Synthesis Yield is Higher than T7 Promoter-Mediated Protein Synthesis.

A strong T7 promoter is commonly used for cellular production of recombinant proteins (Studier et al., 1990). T7 promoter directs also high protein synthesis in cell-free systems when T7 phage RNA polymerase is added to the extracts. Cell-free protein synthesis based on the T7 promoter/T7 RNA polymerase system was compared to the new PargC-driven system by addition of α subunit of *E. coli* RNA polymerase and exogenous RNA polymerase holoenzyme. To perform such a comparison at definite conditions, a sequence which harboured the *B. stearothermophilus* amaA gene was inserted previously downstream the strong T7 promoter in pET3A (Dion et al., 1995) as shown in FIG. 5. Thus, the two plasmids, pETamaA and pPargC8-amaA, differ only from their promoter sequence. Therefore, aminoacylase production observed from the two plasmids reflects the real transcription capacity of T7 and PargC promoters in adequate cell-free systems.

Equimolar concentrations of plasmid DNAs were added to cell-free extracts from *E. coli* BL21 Star RecBCD (DE3) (pRIL) cells and a coupled transcription-translation reaction was carried out at 37° C. for 2 h in the presence of corresponding exogenous RNA polymerase holoenzyme and α subunit. As shown in FIG. 6 and table 3, T7 RNA polymerase, added at a 0.6 u/μl optimal concentration to the reaction mixture, provided nearly 5-fold better protein synthesis than the PargC-driven system performed without addition of exogenous proteins to the reaction. However, the addition of a thermostable RNA polymerase holoenzyme of *T. thermophilus* is sufficient to increase in vitro protein synthesis using the ParyC promoter nearly to the same level. Moreover, much stronger effect was detected by adding the α subunit of *E. coli* RNA polymerase: it provided more than 2.5-fold higher yield by the method of the invention as compared to the T7-mediated system. Finally, the highest protein synthesis level was detected when *T. thermophilus* RNA polymerase holoenzyme and α subunit were added simultaneously to a cell-free system: up to 4-fold better aminoacylase synthesis was observed by the method of the invention as compared to T7 system.

These data revealed that the methods of the invention are more efficient in terms of yield of protein than the T7 phage system.

Thus, using cell-free extracts from genetically modified strains, elongated linear DNAs in combination with the addition of α subunit and/or thermostable RNA polymerase, major improvements were achieved for cell-free protein synthesis in providing a higher yield of functionally active proteins including large ones. In particular, such an improved coupled in vitro transcription-translation system allows the manufacturing of protein arrays for large scale genome analysis. The methods of the invention are particularly appropriate for such applications.

B.7. Semi-Continuous Cell-Free Production of Protein of PargC-Mediated Expression System PargC-mediated expression system with above-mentioned improvements was tested in a semi-continuous cell-free protein synthesis method. Plasmid or PCR-amplified DNA carrying the *B. stearothermophilus* amaA gene was used as a template. Creatine-phosphate was used as an energy source since it was found to be a stable compound for semi-continuous protein synthesis (Kigawa et al., 1999). Synthesis was carried out in 150 μl reaction in dialysis bags at 37° C. overnight in presence or absence of α subunit of *E. coli* RNA polymerase. A radioactive L-methionine was replaced by cold amino acid in *E. coli* BL21 Star RecBCD (DE3) (pRIL) cell-free extracts. 10 μl of samples were used for SDS-PAGE analysis.

As shown in FIG. 9, it was found that aminoacylase production was around 2-fold higher in presence of exogenous α subunit irrespective of the used DNA template. Moreover, a linear PCR-produced DNA template provided nearly the same yield as did a circular pETParg8-amaA plasmid DNA. More than 2 mg/ml of protein were produced using circular or linear DNA templates with the added α subunit Thus, these results show that the method of the invention using cell-free system also provides a high yield of protein synthesis under semi-continuous conditions. This shows that the method is also applicable when a large amount of a desired protein is required.

B. 8. Protein Synthesis in Vitro by Using Cell-Free Extracts Prepared from an *E. coli* Cell Overexpressing RNA Polymerase α Subunit A stimulating effect of adding a pure α subunit in a reaction mixture on in vitro RNA or protein synthesis, without other RNA polymerase's subunits, suggested that a similar effect can be achieved by using cell-free exacts prepared from an *E. coli* cell overexpressing the rpoA gene. Therefore, an experiment was carried out with extracts prepared from *E. coli* BL21 Star (DE3) (pET-rpoA$_{Ec}$) cells after induction of rpoA by IPTG. The extracts were obtained as described above except that expression of the cloned *E. coli* RNA polymerase α subunit was induced by addition of IPTG to a culture at DO$_{600}$=0.6 and incubation was continued up to DO$_{600}$=1.2. In parallel, the same cells are grown without IPTG induction for control.

The data in FIG. 10 and Table 6 show that the cell-free extracts prepared from *E. coli* cells overexpressing α subunit provide much higher protein yield. Almost 16-fold higher synthesis of the aminoacylase was reached with cell-free extracts prepared from the induced cells overexpressing α subunit as compared to cells in which the rpoA gene was not induced. However, when a purified α subunit was added to the reaction mixture, a 5-fold increase of aminoacylase synthesis was detected in cell-free extracts of non-induced cells whereas the added α subunit increased protein synthesis less than twice in cell-free extracts of induced cells.

Thus, these results show that the over-expression of the α subunit in vivo allow the preparation of highly active cell-fee extracts for in vitro protein synthesis.

TABLE 6

Effect of cell-free extracts prepared from cells with or without overexpressed α subunit of *E. coli* RNA polymerase on in vitro protein synthesis.

| N° | IPTG induction of rpoA | Addition of Ec α or CRP | Efficiency of synthesis % |
|---|---|---|---|
| 1 | − | − | 3 |
| 2 | + | − | 47 |
| 3 | − | +Ec α | 15 |
| 4 | + | +Ec α | 82 |
| 5 | − | +CRP | 11 |
| 6 | + | +CRP | 100 |

Conditions used are the same as those described for FIG. 10.

Such stimulating effect of the cell-free extracts prepared from *E. coli* cells overexpressing RNA polymerase α subunit was also detected with the extracts of other *E. coli* strains such as the derivatives of BL21 strain or the *E. coli* XA 4 strain, all these strains carrying pET-rpoA$_{Ec}$.

These data show that in vitro protein synthesis can be improved by supplying cell-free extracts obtained from *E. coli* strains in which the rpoA gene encoding α subunit is overexpressed.

One advantage of the present embodiment is that the use of such cell-free extracts practically excludes the necessity of the addition of an exogenous α subunit of RNA polymerase to the reaction mixture. It simplifies the experimental performance and decreases the total cost of in vitro protein synthesis.

B.9. Transcriptional Regulators in Combination with a Higher Concentration of α Subunit Increase Protein Synthesis in Vivo and in Vitro High aminoacylase synthesis can also be achieved from a derepressed PargC promoter in *E. coli* cells (Savchenko et al., 1998). Indeed, it was found that aminoacylase is produced almost at the same level in *E. coli* cells shifted in a late exponential phase from a rich medium to a minimal medium devoid of L-arginine comparable to the expression from a T7 promoter in IPTG-induced cells carrying a T7 polymerase (see FIG. 9).

Taking into consideration a stimulating effect of the addition of α subunit of RNA polymerase in protein synthesis in vitro, the effect of the overexpression of α subunit of RNA polymerase was also tested on expression of recombinant genes in vivo in *E. coli* cells. The PargC promoter fused to the *B. stearothermophilus* amaA gene was amplified by PCR with Pfu DNA polymerase and cloned into a EcoRV-digested pET21-rpoA plasmid. The resulting plasmids pET21-rpoA-amaA1 and pET21-rpoA-amaA2 acquired the PargC-amaA fusion in two possible orientations (see FIG. 5). Cultures of *E. coli* B21 Star RecBCD (DE3) (pRIL) carrying these plasmids were induced by IPTG, harvested by centrifugation, sonicated and the crude extracts were analysed by SDS-PAGE as described above. It was found, that in vivo induction of α subunit synthesis from a T7 promoter practically had no effect on in vivo expression of the amaA gene irrespective of the orientation of the PargC-amaA fusion in a vector DNA. One of possible interpretations of this negative result could be an influence of another factor on the transcription from the Parg promoter in *E. coli* cells.

Therefore, searching for another potential factor providing a high expression from the *B. stearothermophilus* PargC promoter in *E. coli* cells different growth parameters were first tested. Two *B. stearothermophilus* reporter genes, argC (coding for N-acetylglutamate-5-semialdehyde dehydrogenase) and amaA, both fused to the PargC promoter respectively, in plasmids pHAV2 (Savchenko et al., 1998) and pETParg8-ama (Batisse, 1997, see FIG. 5) were used for in vivo assays. As a control the pBTargC plasmid, in which the argC gene is transcribed from the Ptac promoter (Savchenko et al., 1998), was also used. The hybrid Ptac promoter is considered as a strong promoter for gene expression in viva (De Boer et al., 1983).

Surprisingly, a higher expression of both genes was monitored in cells grown on a M9 minimal medium supplied with 1% glycerol as compared to the growth with 1% glucose (FIG. 11). Similar effect was observed for the argC gene transcribed from the Ptac promoter. This higher expression could be correlated with the increase of the intracellular concentration of cAMP since, in the absence of glucose, this inducer activates the cyclic AMP receptor protein (CRP) which binds the upstream sequence of the *E. coli* lac promoter and stimulates transcription by RNA polymerase (Heyduck et al., 1993). It is known that, in CRP-dependent *E. coli* promoters, transcriptional activation requires interactions between CRP and the α subunit of RNA polymerase (Ebright and Busby, 1995).

Therefore, the effect of CRP on in vitro protein synthesis was tested on a heterologous PargC promoter-mediated expression of the gene encoding aminoacylase.

Aminoacylase protein synthesis was analysed when using various concentrations of the added purified *E. coli* CRP protein to the reaction mixture. A typical example is shown in FIG. 10 which shows a clear increase of aminoacylase production when 100 μg/ml of CRP is added in the reaction mixture containing cell-free extracts prepared from cells without or with induced α subunit of RNA polymerase. The addition of CRP provided a higher protein yield in both extracts at levels comparable with the addition of the RNA polymerase α subunit alone. The addition of the two exogenous proteins together did not give a synergic effect suggesting that the *E. coli* RNA polymerase α subunit and CRP compete for an overlapping sequence in the PargC promoter region.

The results described above show that the concentration of α subunit of RNA polymerase either in vitro or in viva is a crucial determinant in raising protein synthesis in a coupled transcription-translation expression system. Different improvements have been introduced in the present invention which have synergic effects with the increased amount of α subunit for improving the yield and the homogeneity of protein synthesis. These improvements include the use of a PargC promoter of *B. stearothermophilus*, the use of the gene-downstream sequence elongated PCR fragments as DNA templates, the use of PCR fragments elongated with terminator sequences or the use of thermostable RNA polymerase holoenzyme in cell-free expression systems. Moreover, the increased yield of protein synthesis could also be achieved by adding DNA-binding regulatory proteins, like CRP, in a coupled transcription-translational expression system. The described properties of both RNA polymerase α subunit and CRP enlarges the potential application of the improved methods of the invention for protein synthesis in other host in vitro transcription-translation systems. According to the method of the invention, high protein yield can be achieved from other strong promoters including those binding only the RNA polymerase α subunit or only CRP or another DNA-binding regulatory protein in a desired coupled transcription-translation expression system. Furthermore, stimulating effects of the RNA polymerase α subunit on in vitro protein synthesis can be used as a convenient approach for a rapid and efficient identification of strong bacterial promoters. Taken together, these improvements have enabled to increase the yield of model proteins in cell-free expression systems up to 4-fold as compared to currently accessible strong bacteriophage promoter-mediated systems such as the T7 promoter system.

REFERENCES

Ausubel, F. M., Brent, R., Kingston, R. E., Moore, D. D., Seidman, J. G., Smith, J. A. & Struhl, K. (1993). *Current Protocols in Molecular Biology*. John Wiley & Sons, N.Y.

Batisse, N. (1997). Analyse génétique d'enzymes responsables de la résolution des acides aminés de la série L à partir de dérivés N-substiués chez la bactérie thermophile *Bacillus stearothermophilus*. Ph. Thesis, Nantes.

Bowrin, V., Brissette, R., Tsung, K. & Inouye, M. (1994). The α subunit of RNA polymerase specifically inhibits expression of the porin genes ompF and ompC in vivo and in vitro in *Escherichia coli*. *FEMS Microb. Lett.* 115, 1–6.

Bradford, M. M. (1976). A rapid sensitive method for the quantitation of microgram quantities of protein utilising the principle of protein-dye binding. *Anal. Biochem.* 72, 248–254.

De Boer, H. A., Comstock, L. J. & Vasser, M. (1983). The tac promoter: a functional hybrid derived from the trp and lac promoters. *Proc. Natl. Acad. Sci. USA* 80, 21–25.

Dion, M., Loussouam, F., Batisse, N., Rabiller, C. & Sakanyan, V. (1995). Use of the overexpressed *Bacillus stearothermophilus* aminoacylase for the resolution of D,L-amino acids in conventional and non-conventional media. *Biotechnol. Lett.* 17, 905–910.

Dion, M., Chadier, D., Wang, H., Gigot, D., Savchenko, A., Hallet, J.-N., Glansdorff, N. & Sakanyan, V. (1997). The highly thermostable arginine repressor of *Bacillus stearothermophilus*: gene cloning and repressor-operator interactions. *Mol. Microbiol.* 25, 385–398.

Ebright, R. E. & Busby, S. (1995). The *Escherichia coli* RNA polymerase alpha subunit: structure and function. *Curr. Opin. Genet. Dev.* 5, 197–203.

Ehretsmann, L. P., Carpousis, A. J. & Krish, M. M. (1992) mRNA degradation in prokaryotes. *FASEB J* 6, 3186–3192.

Estrem, S. T., Gaal, T., Ross, W. & Gourse, R. L (1998). Identification of an UP element consensus sequence for bacterial promoters. *Proc. Natl. Acad. Sci. USA* 95, 9761–9766.

Gaal, T., Ross. W., Blatter, E. E., Tanh, H., Jia. X, Krishnan, V. V., Assa-Munt, V., Ebright, R. H. & Gourse, R. L (1996). DNA-binding determinants of the α subunit of RNA polymerase: novel DNA-binding domain architecture. *Genes Dev* 10, 16–26.

Georgiou, G. & Valax, P. (1996). Expression of correctly folded proteins in *Escherichia coli*. *Cur. Opinion Biotech.* 7, 190–197.

Gourse, R. L., Ross, W. & Gaal, T. (2000). Ups and downs in bacterial transcription initiation: the role of the alpha subunit of RNA polymerase in promoter recognition. *Mol. Microbiol.* 37, 687–695.

Gross, J. D., Lonetto, M. & Losick, R. (1992). In: Transcriptional Regulation. (Yamamoto, K & McKnight, S. eds) pp. 129–176. Cold Spring Harbor Laboratory, New York.

Ho, N. S., Hunt, D. H., Horton, M. R., Pullen K. J. & Pease R., L. (1989). Site directed mutagenesis by overlap extension using the polymerase chain reaction. *Gene* 77, 51–59.

Ishihama A. (1993). Protein-protein communication within the transcription apparatus. *J Bacteriol.* 175, 2483–2489.

Jeon, Y. H., Yamazaki, T., Otomo, T., Ishihama, A. & Kyogoku, Y. (1997). Flexible linker in the RNA polymerase alpha subunit facilitates the independent motion of the C-terminal activator contact domain. *J. Mol. Biol.* 267, 953–962.

Kigawa, T., Yabuki, T., Yoshida, Y., Tsutsui, M., Ito, Y., Shibata, T. & Yokoyama, S. (1999). Cell-free production and stable-isotope labeling of milligram quantities of proteins. *FEBS Letters* 442, 15–19.

Kim, D.-M. & Swartz, J. R. (1999). Prolonging cell-free protein synthesis with a novel ATP regeneration system. *Biotech. & Bioengin.* 66, 180–188.

Lesley, S. S., Borw, M. A. & Burgess, R. R. (1991). Use of in vitro protein synthesis from polymerase chain reaction-generated templates to study interaction of *Escheschia coli* transcription factors with core RNA polymerase and for epitope mapping of monoclonal antibodies. *J. Biol. Chem.* 266, 2632–2638.

Miller, J. H. (1992). A short course in bacterial genetics. Cold Spring Harbor, N.Y.: Cold Spring Harbor Laboratory.

Murphy, K. (1998). Use of bacteriophage λ recombination functions to promote gene replacement in *Escherichia coli*. *J. Bacteriol.* 180, 2062–2071.

Pelham, H. R. & Jackson, R. J. (1976). An efficient mRNA-dependent translation system from reticulocyte lysates. *Eur. J. Biochem.* 67, 247–256.

Roberts, B. E. & Paterson, B. M. (1973). Efficient translation of tobacco mosaic virus RNA and rabbit globin 9S RNA in a cell-free system from commercial wheat germ. *Proc. Natl. Acad. Sci. USA* 70, 2330–2334.

Ross, W., Gosink, K. K., Salomon, J., Igarashi, K., Zou, C., Ishihama, A, Severinov, K. & Gourse, R. L. (1993). A third recognition element in bacterial promoters: DNA binding by the α subunit of RNA polymerase. *Science* 262, 1407–1413.

Ross, W., Alyar, S. E., Salomon, J. & Gourse, R. L. (1998). *Escherichia coli* promoters with UP elements of different strengths: modular structure of bacterial promoters. J Bacteriol 180, 5375–5383

Sakanyan, V. A., Hovsepyan, A. S., Mett, I. L., Kochikyan, A. V. & Petrosyan, P. K. (1990). Molecular cloning and structural-functional analysis of arginine biosynthesis genes of the thermophilic bacterium *Bacillus stearothermophilus*. *Genetika* (USSR) 26, 1915–1925.

Sakanyan, V., Charlier, D., Legrain, C., Kochikyan, A., Mett, I., Piérard, A. & Glansdorff, N. (1993a). Primary structure, partial purification and regulation of key enzymes of the acetyl cycle of aginine biosynthesis in *Bacillus stearothermophilus*: dual function of ornithine acetyltransferase. *J. Gen. Microbiol.* 139, 393–402.

Sakanyan, V., Desmarez, L., Legrain, C., Charlier, D., Mett, I., Kochikyan, A., Savchenko, A., Boyen, A., Falmagne, P., Piérard, A & Glansdorff. N. (1993b). Gene cloning, sequence analysis, purification, and characterization of a thermostable aminoacylase from *Bacillus stearothermophilus*. *Appl. Environ. Microbiol.* 59, 3878–3888.

Savchenko, A., Charlier, D., Dion, M., Weigel, P., Hallet, J.-N., Holtham, C., Baumberg, S., Glansdorff, N. & Sakanyan, V. (1996). The arginine operon of *Bacillus stearothermophilus*: characterization of the control region and its interaction with the heterologous B. subtilis arginine repressor. *Mol. Gen. Genet.* 252, 69–78.

Savchenko A., Weigel P., Dimova D., Lecocq M. & Sakanyan V. (1998). The *Bacillus stearothermophilus* argCJBD operon harbours a strong promoter as evaluated in *Escherichia coli* cells. Gene 212, 167–177.

Spitzer S. & Eckstein F. (1988). Inhibition of deoxyribonucleases by phosphorothioate groups in oligodeoxyribonucleotides. *Nucleic Acids Res.* 16, 11691–11704.

Studier, F. W., Rosenberg, A. H., Dunn, J. J. & Dubendorff, J. W. (1990). Use of T7 RNA polymerase to direct expression of cloned genes. Methods Enzymol. 185, 60–89.

Zawadski, V. & Gross, H. J. (1991). Rapid and simple purification of T7 RNA polymerase. *Nucl. Acids Res.* 19, 1948.

Zubay, G. (1973). In vitro synthesis of protein in microbial systems. *Ann. Rev. Genet* 7, 267–287.

The invention claimed is:

1. A method to increase RNA synthesis from a DNA template comprising:
   a) providing a cell-free system comprising a bacterial cell-free extract;
   b) adding a DNA template comprising a bacterial promoter with at least one UP element to said cell free system; and
   c) recovering the synthesized RNA,
   wherein the ratio of an α subunit of RNA polymerase to other subunits concentration in said cell-free system is increased as compared to the conventional ratio of two α, one β, one β', and one σ.

2. The method according to claim 1, wherein the bacterial promoter is an argC gene promoter of *Bacillus stearothermophilus*.

3. The method according to claim 2, wherein the promoter comprises the sequence from nucleotide at position –89 to nucleotide at position +1 of the argC gene promoter of *Bacillus stearothermophilus*, when position +1 is the first nucleotide in mRNA of the argC gene.

4. The method according to claim 1, wherein said cell-free system further comprises a purified thermostable RNA polymerase holoenzyme.

5. The method according to claim 4, wherein said thermostable RNA polymerase holoenzyme is from *Thermus thermophilus*.

6. The method according to claim 1, wherein the concentration of said α subunit of RNA polymerase is increased by adding a purified α subunit of RNA polymerase to the bacterial cell-free extract.

7. The method according to claim 6, wherein said purified α subunit is added to a final concentration between 15 μg/ml and 200 μg/ml.

8. The method according to claim 6, wherein said purified added α subunit of RNA polymerase is different from an α subunit present in the bacterial extract.

9. The method according to claim 8, wherein said purified added α subunit is from *E. coli, T. maritima* or *T. neapolitana*.

10. The method according to claim 6, wherein the purified added α subunit is purified from cells overexpressing a gene encoding an α subunit of RNA polymerase.

11. The method according to claim 1, wherein the bacterial cell-free extract is prepared from cells overexpressing a gene encoding an α subunit of RNA polymerase.

12. The method according to claim 1, wherein the UP element is a AT-rich region around 18–20 bp long.

13. The method according to claim 1, wherein said bacterial cell-free extract is from *E. coli* cells.

14. The method according to claim 13, wherein said *E. coli* cells are K12 A19 cells having a rna19 gdhA2 his-95 relA11 spoT1metB1 genotype.

15. A method to increase the production of a protein from a DNA template in a cell-free system comprising:
   a) providing in a reaction mixture, a bacterial cell-free system;
   b) adding to the reaction mixture the DNA template encoding a desired protein and a purified α subunit of a RNA-polymerase; and
   c) recovering the produced protein,
   wherein the DNA template comprises a bacterial promoter with at least one UP element.

16. The method according to claim 15, wherein said purified α subunit is added to a final concentration between 15 μg/ml and 200 μg/ml.

17. The method according to claim 15, wherein a DNA-binding regulatory protein is further added to the reaction mixture at step (b).

18. The method according to claim 15, wherein said DNA template comprises an amplification product of an Open Reading Frame encoding the desired protein.

19. The method according to claim 18, wherein said DNA template further comprises an additional DNA fragment, which is at least 3 bp long, located immediately downstream of the stop codon of said Open Reading Frame.

20. The method according to claim 18, wherein said DNA template further comprises an additional DNA fragment containing a transcriptional terminator.

21. The method according to claim 20, wherein said transcriptional terminator is a T7 phage transcriptional terminator.

22. The method according to claim 20, wherein said additional DNA fragment is longer than 100 bp.

23. The method according to claim 20, wherein said additional DNA fragment is longer than 200 bp.

24. The method according to claim 15, wherein a thermostable RNA polymerase is further added in step b).

25. The method according to claim 24, wherein said added RNA polymerase is a thermostable RNA polymerase from *T. thermophilus*.

26. The method according to claim 15, wherein the bacterial promoter with at least one UP element is from the argC gene of *Bacillus stearothermophilus*.

27. The method according to claim 26, wherein the bacterial promoter includes the sequence from nucleotide at position −89 to nucleotide at position +1 of the argC gene promoter of *Bacillus stearothermophilus*, when position +1 is the first nucleotide in mRNA of the argC gene.

28. A method for RNA or polypeptide synthesis from a DNA template comprising:

a) providing a bacterial cell-free extract;
b) adding a DNA template comprising a bacterial promoter with at least one UP element to said cell extract, and
c) recovering the synthesized RNA or polypeptide;
wherein the ratio of an α subunit of RNA polymerase to other subunits concentration in said cell-free extract is increased as compared to the conventional ratio of two α, one β, one β', and one σ, by adding in said bacterial cell free extract a purified α subunit of RNA polymerase prepared from cells overexpressing a gene encoding said α subunit of RNA polymerase.

* * * * *